US011352457B2

(12) United States Patent
Nakamura et al.

(10) Patent No.: US 11,352,457 B2
(45) Date of Patent: Jun. 7, 2022

(54) FLUORINE-CONTAINING COMPOUND HAVING UNSATURATED BOND, AND SURFACE MODIFIER USING THE SAME

(71) Applicant: TOSOH FINECHEM Corporation, Shunan (JP)

(72) Inventors: Shinichiro Nakamura, Shunan (JP); Norihisa Kondo, Shunan (JP); Takayuki Yamasaki, Shunan (JP); Tomohiro Shirai, Shunan (JP)

(73) Assignee: TOSOH FINECHEM CORPORATION, Shunan (JP)

( * ) Notice: Subject to any disclaimer, the term of this patent is extended or adjusted under 35 U.S.C. 154(b) by 879 days.

(21) Appl. No.: 16/025,014

(22) Filed: Jul. 2, 2018

(65) Prior Publication Data
US 2018/0305484 A1    Oct. 25, 2018

Related U.S. Application Data

(63) Continuation of application No. PCT/JP2016/088961, filed on Dec. 27, 2016.

(30) Foreign Application Priority Data

Jan. 8, 2016  (JP) .............................. JP2016-002872
Mar. 8, 2016  (JP) .............................. JP2016-044421

(51) Int. Cl.
| | |
|---|---|
| C08F 220/14 | (2006.01) |
| B29C 33/60 | (2006.01) |
| C03C 17/28 | (2006.01) |
| C03C 17/32 | (2006.01) |
| C07C 21/18 | (2006.01) |
| C07C 21/19 | (2006.01) |
| C07C 21/215 | (2006.01) |
| C07C 33/42 | (2006.01) |
| C07C 69/54 | (2006.01) |
| C07C 69/653 | (2006.01) |
| C07F 7/12 | (2006.01) |
| C07F 7/18 | (2006.01) |
| C07F 9/09 | (2006.01) |
| C09D 133/16 | (2006.01) |
| C09K 3/18 | (2006.01) |

(52) U.S. Cl.
CPC ............ *C08F 220/14* (2013.01); *B29C 33/60* (2013.01); *C03C 17/28* (2013.01); *C03C 17/328* (2013.01); *C07C 21/18* (2013.01); *C07C 21/19* (2013.01); *C07C 21/215* (2013.01); *C07C 33/423* (2013.01); *C07C 69/54* (2013.01); *C07C 69/653* (2013.01); *C07F 7/12* (2013.01); *C07F 7/1804* (2013.01); *C07F 9/091* (2013.01); *C09D 133/16* (2013.01); *C09K 3/18* (2013.01); *C03C 2218/111* (2013.01); *C03C 2218/116* (2013.01)

(58) Field of Classification Search
CPC ....... C08F 220/14; B29C 33/06; C03C 17/28; C03C 17/328; C03C 2218/111; C03C 2218/116; C07C 21/18; C07C 21/19; C07C 21/215; C07C 33/423; C07C 69/54; C07C 69/653; C07F 7/12; C07F 7/1804; C07F 9/091; C09D 133/16; C09K 3/18
USPC ......................................................... 526/245
See application file for complete search history.

(56) References Cited

U.S. PATENT DOCUMENTS

| | | | | |
|---|---|---|---|---|
| 3,901,948 | A * | 8/1975 | Riess ...................... | C07C 21/18 260/653.3 |
| 5,243,025 | A | 9/1993 | Farnham et al. | |
| 5,820,665 | A | 10/1998 | Kai | |
| 8,481,660 | B2 | 7/2013 | Murata et al. | |
| 2010/0292393 | A1* | 11/2010 | Murata ................... | C08F 18/20 526/245 |
| 2011/0315050 | A1* | 12/2011 | Sato ......................... | B28B 7/36 106/38.22 |

FOREIGN PATENT DOCUMENTS

| | | | | |
|---|---|---|---|---|
| JP | 49-117410 A | 11/1974 | | |
| JP | 54-41822 A | 4/1979 | | |
| JP | 54041822 A | * 4/1979 | ............... | C07F 9/09 |
| JP | 58-180597 A | 10/1983 | | |
| JP | 58180597 A | * 10/1983 | ............. | B29B 13/00 |
| JP | 03-041162 A | 2/1991 | | |
| JP | 04-346948 A | 12/1992 | | |

(Continued)

OTHER PUBLICATIONS

JP2014-040373-A—machine translation (Year: 2014).*
JPS58-180597-A—machine translation (Year: 1983).*
JP H05-194560-A—machine translation (Year: 1993).*
JPS54-41822-A—machine translation (Year: 1979).*
Korean Office Action dated Jun. 25, 2019 for the Korean Patent Application No. 10-2018-7019252.
Communication pursuant to Article 94(3) EPC dated Sep. 29, 2020 for European Patent Application No. 16883870.4.
United States Environmental Protection Agency, "Risk Management for Per- and Polyfluoroalkyl Substances (PFAS) under TSCA" (Retrieved from the Internet on Jan. 10, 2020).

(Continued)

*Primary Examiner* — Ling Siu Choi
*Assistant Examiner* — Ronald Grinsted
(74) *Attorney, Agent, or Firm* — Volpe Koenig

(57) ABSTRACT

To provide a novel fluorine-containing compound that does not include any long chain perfluoroalkyl unit having 8 or more carbon atoms, which is problematic in terms of the environment, and that is excellent in water repellency/oil repellency, and a surface modifier using the compound. [Solution] There are used a fluorine-containing compound represented by the following general formula (1), the following general formula (2) or the following general formula (5): $Rf^1-(CR^1=CR^2-X-Rf^2)_n-Y-Z$ (1), $Rf^1-(X-CR^1=CR^2-Rf^2)_n-Y-Z$ (2) or $Rf^3-(CF=CR^3-CR^4=CF-Rf^4)_n-Y-Z$ (5); and a surface modifier using the compound.

16 Claims, No Drawings

(56) References Cited

FOREIGN PATENT DOCUMENTS

| | | | | |
|---|---|---|---|---|
| JP | 04-346956 | A | 12/1992 | |
| JP | 05-194560 | A | 8/1993 | |
| JP | 05-214029 | A | 8/1993 | |
| JP | 5194560 | A * | 8/1993 | ............... C07F 9/09 |
| JP | 06-184352 | A | 7/1994 | |
| JP | 06-248026 | A | 9/1994 | |
| JP | 2006-160933 | A | 6/2006 | |
| JP | 2010-215518 | A | 9/2010 | |
| JP | 2010215518 | A * | 9/2010 | ............... C07F 9/38 |
| JP | 5146455 | B | 2/2013 | |
| JP | 2014-040373 | A | 3/2014 | |
| JP | 2014040373 | A * | 3/2014 | ............ C03C 17/30 |
| KR | 10-1137286 | B1 | 4/2012 | |
| WO | 2009/087981 | A1 | 7/2009 | |
| WO | 2009/093568 | A1 | 7/2009 | |
| WO | WO-2009093568 | A1 * | 7/2009 | ............ C07C 67/08 |
| WO | 2009/151109 | A1 | 12/2009 | |

OTHER PUBLICATIONS

The Danish Environmental Protection Agency, Part 4.1.4—Bioaccumulation, from "Short-chain Polyfluoroalkyl Substances (PFAS)." (2015).
The Danish Environmental Protection Agency, "Short-chain Polyfluoroalkyl Substances (PFAS)." (2015).
Extended European Search Report dated Jul. 16, 2019 for the European Patent Application No. 16883870.4.
Sablina et al., "The Role of Multiple Bonds in the Radiolysis of Linear Perfluorocarbons," Mendeleev Communications, vol. 2, Issue 4, pp. 141-143 (1992).
Allayarov et al., "Radiolysis of n-perfluoroalkanes and polytetrafluoroethylene," Journal of Fluorine Chemistry vol. 96, Issue 1, pp. 61-64 (Jun. 24, 1999).
Yang et al., "A novel double insertion of the difluoromethylene unit from trifluoromethylcopper into the carbon-copper bond of perfluoroaryl- and perfluorovinylcopper reagents: preparation, mechanism and applications of new fluorinated copper reagents," Journal of Fluorine Chemistry vol. 102, Issues 1-2, pp. 89-103 (Mar. 2000).

* cited by examiner

FLUORINE-CONTAINING COMPOUND HAVING UNSATURATED BOND, AND SURFACE MODIFIER USING THE SAME

This application claims the benefit of Japanese Patent Application No. 2016-044421, filed Mar. 8, 2016, and Japanese Patent Application No. 2016-002872, filed Jan. 8, 2016, the contents of which are hereby incorporated by reference herein.

TECHNICAL FIELD

The present invention relates to a novel fluorine-containing compound having an unsaturated bond, which is useful as a raw material of a surface modifier or the like.

BACKGROUND ART

Fluorine has unique properties such as a high electronegativity and a low polarizability, and is used as an element useful for functional materials utilizing properties such as heat resistance, chemical resistance, water repellency/oil repellency, a low friction property and a low refraction property.

A compound having a perfluoroalkyl group having 8 or more carbon atoms, however, has been heretofore used for functional products imparting water repellency and/or oil repellency, but such a compound has been problematic in terms of accumulation in the environment and the human body, and hazardousness.

Therefore, studies about substitution with a compound having a perfluoroalkyl group having 6 or less carbon atoms have been conducted, and it is known that, as the carbon chain of perfluorocarbon is shorter, the water-repellent/oil-repellent performance is worse than that of a conventional compound having a perfluoroalkyl group having 8 or more carbon atoms.

As a method for improving the water repellency/oil repellency of a material having a perfluoroalkyl group having 6 or less carbon atoms, an example is known where a group producing various interactions between respective bonding groups of a fluoro-containing group and a substrate is introduced (see, for example, Patent Document 1).

A method is also known which includes forming a compound having a perfluoroalkyl group whose fluorine is partially replaced with hydrogen, and thus using the compound as a structure of a perfluoroalkyl group unit having 6 or less carbon atoms, which is deemed to be low in accumulation in the living body, for a modifier (see, for example, Patent Document 2 and Patent Document 3).

There is also known use of an alternative material having a perfluoropolyether structure, such as Optool (registered trademark).

Although many surface modifiers including a perfluoroalkyl group have been thus found, there has not been known any one where the structure of such a modifier includes an unsaturated bond and there has also not been known any example where a fluorine-containing modifier includes an unsaturated bond therein to thereby improve surface modification performance.

PRIOR ART DOCUMENT

Patent Document

Patent Document 1: International Publication No. WO 2009/087981

Patent Document 2: Japanese Patent No. 5146455
Patent Document 3: Japanese Patent Laid-Open No. 2014-040373

SUMMARY OF THE INVENTION

Problems to be Solved by the Invention

The present invention provides a novel fluorine-containing compound serving as a new material exerting excellent, high water-repellent and oil-repellent effects and having an enhanced surface modification performance as compared with a conventional one, as well as a surface modifier using the compound.

Means for Solving the Problems

The present inventors have found that a compound containing a fluorine-containing long-chain group having an unsaturated bond, shown below, is used for surface modification to result in a high water-repellent and oil-repellent performance, thereby leading to completion of the present invention.

That is, the present invention is an invention according to a fluorine-containing compound represented by the following general formula (1) or the following general formula (2), or the following general formula (5):

$$Rf^1-(CR^1=CR^2-X-Rf^2)_n-Y-Z \quad (1)$$

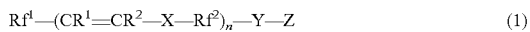

$$Rf^1-(X-CR^1=CR^2-Rf^2)_n-Y-Z \quad (2)$$

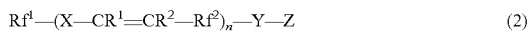

wherein in the formula (1) or in the formula (2),
$Rf^1$ represents a perfluoroalkyl group having 1 to 6 carbon atoms, with a $CF_3$ terminal,
$Rf^2$ represents a perfluoroalkylene group having 1 to 6 carbon atoms,
$R^1$ and $R^2$ each independently represent a hydrogen atom or a fluorine atom,
n represents an integer of 1 to 5,
X is absent in the formula (1) or in the formula (2), or represents $CH_2$, O or S,
Y represents a linking group, and
Z represents any structure of the following (i) to (iii):
(i) a structure represented by the following general formula (3) or the following general formula (4):

$$-P(=O)(OM^1)(OM^2) \quad (3)$$

$$-O-P(=O)(OM^1)(OM^2) \quad (4)$$

wherein in the formula (3) or in the formula (4), $M^1$ and $M^2$ each independently represent a hydrogen atom, an ammonium salt, an organic amine salt, or an alkyl group having 1 to 4 carbon atoms;
(ii) a polymerizable group; or
(iii) $SiL_kL'_{(3-k)}$ wherein L represents a hydrolyzable group or a hydroxyl group, L' represents a hydrocarbon group having 1 to 6 carbon atoms, k represents an integer of 1 to 3, and, when a plurality of L and L' groups are present, the L and L' groups may be different from or the same as each other.

In addition, the present invention relates to the fluorine-containing compound wherein $Rf^2$ represents a linear perfluoroalkylene group having 1 to 6 carbon atoms:

$$Rf^3-(CF=CR^3-CR^4=CF-Rf^4)_n-Y-Z \quad (5)$$

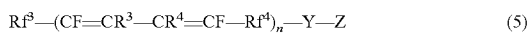

wherein in the formula (5),
$Rf^3$ represents a perfluoroalkyl group having 1 to 5 carbon atoms, with a $CF_3$ terminal, $Rf^4$ represents a perfluoroalkylene group having 1 to 5 carbon atoms, $R^3$ and $R^4$ each independently represent a hydrogen atom or a fluorine atom, n represents an integer of 1 to 5, Y represents a linking group, and Z represents any structure of the following (i) to (iii):

(i) a structure represented by the following general formula (6) or the following general formula (7):

$$—P(=O)(OM^3)(OM^4) \quad (6)$$

$$—O—P(=O)(OM^3)(OM^4) \quad (7)$$

wherein in the formula (6) or in the formula (7), $M^3$ and $M^4$ each independently represent a hydrogen atom, an ammonium salt, an organic amine salt, or an alkyl group having 1 to 4 carbon atoms;

(ii) a polymerizable group; or (iii) $SiL_kL'_{(3-k)}$ wherein L represents a hydrolyzable group or a hydroxyl group, L' represents a hydrocarbon group having 1 to 6 carbon atoms, k represents an integer of 1 to 3, and, when a plurality of L and L' groups are present, the L and L' groups may be different from or the same as each other.

In addition, the present invention relates to the fluorine-containing compound described above wherein $Rf^4$ represents a linear perfluoroalkylene group having 1 to 5 carbon atoms.

In addition, the present invention relates to the fluorine-containing compound wherein Y is represented by the following general formula (8):

$$(CH_2)_l—Q—(CH_2)_m \quad (8)$$

wherein in the formula (8), the sum of l and m is an integer of 2 to 6;

when l and/or m represents 2 or more, a —CH=CH— structure is optionally included instead of —$CH_2CH_2$—; and Q is absent in the formula (8), or represents —OCONH—, —CONH—, —O—, —NH—, —CO—O—, —O—CO—, —NHCONH— or —$C_6H_4$—.

In addition, the present invention relates to the fluorine-containing compound wherein $R^1$ and/or $R^2$ represent(s) a hydrogen atom, and $R^3$ and/or $R^4$ represent(s) a hydrogen atom.

In addition, the present invention relates to the fluorine-containing compound wherein X is absent in the formula (1) or in the formula (2), or represents $CH_2$.

In addition, the present invention relates to the fluorine-containing compound wherein the hydrolyzable group L represents Cl or $OR^5$ wherein $R^5$ represents an alkyl group having 1 to 4 carbon atoms.

In addition, the present invention relates to a surface modifier comprising the novel fluorine compound described above.

Hereinafter, the present invention will be described in detail.

The fluorine-containing compound of the present invention is represented by the following general formula (1) or the following general formula (2).

$$Rf^1—(CR^1=CR^2—X—Rf^2)_n—Y—Z \quad (1)$$

$$Rf^1—(X—CR^1=CR^2—Rf^2)_n—Y—Z \quad (2)$$

Here, in the general formula (1) and in the general formula (2), an $Rf^1$ group is a perfluoroalkyl group having 1 to 6 carbon atoms, with a $CF_3$ terminal. While the structure may have a branched structure, it is considered that a linear perfluoroalkyl group easily has a self-assembled structure to easily form a monolayer on a glass surface, and therefore a linear perfluoroalkyl group is preferable. In addition, an $Rf^2$ group is a perfluoroalkylene group having 1 to 6 carbon atoms. While the structure may have a branched structure, a linear perfluoroalkylene group is preferable.

Specific structures of the portion $Rf^1—(CR^1=CR^2—X—Rf^2)_n—$ in the general formula (1) and the general formula (2) include $C_2F_5—CH=CH—C_4F_8—$, $C_2F_5—CH=CF—C_4F_8—$, $C_2F_5—CF=CH—C_4F_8—$, $C_2F_5—CF=CF—C_4F_8—$, $C_2F_5—(CH=CH—C_4F_8)_2—$, $C_2F_5—(CH=CH—C_4F_8)_3—$, $C_2F_5—CH=CH—C_6F_{12}—$, $C_4F_9—CH=CH—C_4F_8—$, $C_4F_9—CH=CH—C_6F_{12}—$, $C_6F_{13}—CH=CH—C_4F_8—$, $C_6F_{13}—CH=CH—C_6F_{12}—$, $C_2F_5—CH=CH—C_4F_8—$, $CF_3—CF=CHCH_2C_4F_8—$, $CF_3—CF=CHCH_2C_6F_{12}—$, $C_3F_7—CF=CHCH_2C_4F_8—$, $C_3F_7—CF=CHCH_2C_6F_{12}—$, $C_5F_{11}—CF=CHCH_2C_4F_8—$, $C_5F_{11}—CF=CHCH_2C_6F_{12}—$, $C_2F_5—CH_2CH=CF—C_3F_6—$, $C_2F_5—CH_2CH=CF—C_5F_{10}—$, $C_4F_9—CH_2CH=CF—C_3F_6—$, $C_4F_9—CH_2CH=CF—C_5F_{10}—$, $C_6F_{13}—CH_2CH=CF—C_3F_6—$, $C_6F_{13}—CH_2CH=CF—C_5F_{10}—$, $C_6F_{13}—(CH_2CH=CF—C_3F_6)_2—$, and $C_6F_{13}—(CH_2CH=CF—C_3F_6)_3—$.

Such structures can be each obtained by performing radical addition of an iodinated compound in the form of a combination of $Rf^1—I$ and $CHR^1=CR^2—Rf^2—I$, or $Rf^1—CR^1=CHR^2$ and $I—Rf^2—I$, or the like, and thereafter subjecting a structural portion of —$CF_2$—$CIR^1$—$CHR^2CF_2$— generated, to an HI-elimination or IF-elimination reaction.

A terminal iodine located opposite to the $Rf^1$ end can be treated with a proper reagent to thereby introduce a group such as olefin, alcohol or amine. The "terminal iodine located opposite to the $Rf^1$ end" here means, for example, I (iodine) adjacent to $C_4F_8$ in the case of $C_6F_{13}—CH=CH—C_4F_8—I$, and means an unreacted terminal iodine remaining after the addition reaction, located at the $Rf^2$ side.

For example, in the case of a compound obtained by HI-elimination of $Rf^1—CIR^1—CHR^2—Rf^2—I$, the resulting $Rf^1—CR^1=CR^2—Rf^2—I$ can be subjected to addition with ethylene, $Rf^1—CR^1=CR^2—Rf^2—CH_2CH_2I$ consequently obtained can be hydrolyzed to synthesize $Rf^1—CR^1=CR^2—Rf^2—CH_2CH_2OH$, and thereafter $Rf^1—CR^1=CR^2—Rf^2—CH_2CH_2OH$ can be bound to a proper introduction material of a Z group, such as chlorophosphoric acid ester, acryloyl chloride or isocyanate group-containing trialkoxysilane according to a known method to thereby provide a fluorine-containing compound of interest.

In the general formula (1) and the general formula (2), preferably, $R^1$ and $R^2$ each independently represent a hydrogen atom or a fluorine atom and n represents an integer of 1 to 5. Further preferably, $R^1$ and/or $R^2$ represent(s) a hydrogen atom.

Preferably, X is absent in the general formula (1) or the general formula (2), or represents $CH_2$, O or S. That is, X can impart high improvement performance, even when X is absent or represents $CH_2$, O or S, as long as an olefin compound represented by the general formula (1) or the general formula (2) is obtained.

Specifically, when X is absent, the general formula (1) and the general formula (2) each represent $Rf^1—(CR^1=CR^2—Rf^2)_n—Y—Z$. In addition, in an example where X represents $CH_2$, the formula (1) represents $Rf^1—(CR^1=CR^2—CH_2—Rf^2)_n—Y—Z$ and the formula (2) represents $Rf^1—(CH_2—CR^1=CR^2—Rf^2)_n—Y—Z$.

The synthesis method in the case of the absence of X is, for example, as follows: $Rf^1—I$ and $CHR^1=CR^2—Rf^2—I$, or $Rf^1—CR^1=CHR^2$ and $I—Rf^2—I$ can be subjected to radical addition and thereafter HI-elimination to thereby synthesize $Rf^1—CR^1=CR^2—Rf^2—I$.

In addition, the synthesis method in the case of X representing $CH_2$ is, for example, as follows: $Rf^1—CFR^1—CR^2=CH_2$ and $I—Rf^2—I$, or $Rf^1—I$ and $CH_2=CHR^1—CFR^2—Rf^2—I$ can be subjected to radical addition and thereafter an IF-elimination reaction to thereby synthesize $Rf^1—CR^1=CR^2—CH_2—Rf^2—I$ or $Rf^1—CH_2—CR^1=CR^2—Rf^2—I$, respectively.

Furthermore, a compound where X=O or S can be obtained by dehydrohalogenation of a compound represented by $Rf^1—X—CR^1R^3—CR^2R^4—Rf^2—I$ or $Rf^1—CR^1R^3—CR^2R^4—X—Rf^2—I$ (one of $R^3$ and $R^4$ represents H and the other thereof represents an element selected from Cl, Br and I).

Z in the general formula (1) and the general formula (2) represents a surface modification group represented by the following general formula (3) or the following general formula (4).

$$—P(=O)(OM^1)(OM^2) \quad (3)$$

$$—O—P(=O)(OM^1)(OM^2) \quad (4)$$

Here, in the general formula (3) or in the general formula (4), $M^1$ and $M^2$ each independently represent a hydrogen atom, an ammonium salt, an organic amine salt, or an alkyl group having 1 to 4 carbon atoms.

In addition, the fluorine-containing compound of the present invention is represented by the following general formula (5):

$$Rf^3—(CF=CR^3—CR^4=CF—Rf^4)_n—Y—Z \quad (5)$$

Here, in the general formula (5), an $Rf^3$ group is a perfluoroalkyl group having 1 to 5 carbon atoms, with a $CF_3$ terminal. While the structure may have a branched structure, it is considered that a linear perfluoroalkyl group easily has a self-assembled structure to easily form a monolayer on a glass surface, and therefore a linear perfluoroalkyl group is preferable. In addition, an $Rf^4$ group is a perfluoroalkylene group having 1 to 5 carbon atoms. While the structure may have a branched structure, a linear perfluoroalkylene group is preferable.

Specific structures of the portion $Rf^3—(CF=CR^3—CR^4=CF—Rf^4)_n—$ in the general formula (5) include $CF_3—CF=CH—CH=CF—C_3F_6—$, $CF_3—CF=CH—CH=CF—C_5F_{10}—$, $C_3F_7—CF=CH—CH=CF—C_3F_6—$, $C_3F_7—CF=CH—CH=CF—C_5F_{10}—$, $C_5F_{11}—CF=CF—CH=CF—C_5F_{10}—$, $C_5F_{11}—CF=CH—CF=CF—C_5F_{10}—$, $C_5F_{11}—CF=CF—CF=CF—C_5F_{10}—$, $C_5F_{11}—CF=CH—CH=CF—C_3F_6—$, $C_5F_{11}—CF=CH—CH=CF—C_5F_{10}—$, $CF_3—(CF=CH—CH=CF—C_5F_{10})_2—$, $C_3F_7—(CF=CH—CH=CF—C_5F_{10})_2—$, $C_5F_{11}—(CF=CH—CH=CF—C_5F_{10})_2—$.

Such structures can be each obtained by performing radical addition of an iodine compound in the form of a combination of $Rf^3—CF_2—I$ and $CHR^3=CR^4—CF_2—Rf^4—I$, or $Rf^3CF_2—CR^3=CHR^4$ and $I—CF_2—Rf^4—I$, or the like and thereafter subjecting a structural portion of $—CF_2—CIR^3—CHR^4CF_2—$ generated, to an HI-elimination or IF-elimination reaction.

A terminal iodine located opposite to the $Rf^3$ end can be treated with a proper reaction test material to thereby introduce a group such as olefin, alcohol or amine. The "terminal iodine located opposite to the $Rf^3$ end" here means, for example, I (iodine) adjacent to $C_5F_{10}$ in the case of $C_5F_{11}—CF=CH—CH=CF—C_5F_{10}—I$, and means an unreacted terminal iodine remaining after the addition reaction, located closer to $Rf^4$.

For example, in the case of a compound obtained by IF-elimination of $Rf^3—CF_2—CIR^3—CHR^4—CF_2—Rf^4—I$, the resulting $Rf^3—CF=CR^3—CHR^4—CF_2—Rf^4—I$ can be further subjected to HF-elimination to provide $Rf^3—CF=CR^3—CR^4=CF—Rf^4—I$, thereafter $Rf^3—CF=CR^3—CR^4=CF—Rf^4—I$ can be further subjected to addition with ethylene, the resulting $Rf^3—CF=CR^3—CR^4=CF—Rf^4—CH_2CH_2I$ can be hydrolyzed to synthesize $Rf^3—CR^3=CR^4—Rf^4—CH_2CH_2OH$, and thereafter $Rf^3—CR^3=CR^4—Rf^4—CH_2CH_2OH$ can be bound to a proper introduction material of a Z group, such as chlorophosphoric acid ester, acryloyl chloride or isocyanate group-containing trialkoxysilane according to a known method to thereby provide a fluorine-containing compound of interest.

In the general formula (5), preferably, $R^3$ and $R^4$ each independently represent a hydrogen atom or a fluorine atom and n represents an integer of 1 to 5. Further preferably, $R^3$ and/or $R^4$ represent(s) a hydrogen atom.

Z in the general formula (5) represents a surface modification group represented by the following general formula (6) or the following general formula (7).

$$—P(=O)(OM^3)(OM^4) \quad (6)$$

$$—O—P(=O)(OM^3)(OM^4) \quad (7)$$

Here, in the general formula (6) or in the general formula (7), $M^3$ and $M^4$ each independently represent a hydrogen atom, an ammonium salt, an organic amine salt, or an alkyl group having 1 to 4 carbon atoms.

Such a functional group having an olefin structure sandwiched between perfluoroalkyl chains can be bound to a surface modification group Z via a linking group Y also serving as a spacer portion, thereby synthesizing a compound of interest.

The linking group Y is represented by the following general formula (8).

$$(CH_2)_l—Q—(CH_2)_m \quad (8)$$

Here, in the general formula (8), the sum of l and m is an integer of 2 to 6; and when l and/or m represents 2 or more, a $—CH=CH—$ structure is optionally included instead of $—CH_2CH_2—$.

Q is absent in the general formula (8), or represents $—OCONH—$, $—CONH—$, $—O—$, $—NH—$, $—CO—O—$, $—O—CO—$, $—NHCONH—$ or $—C_6H_4—$. When Q here represents $—C_6H_4—$, examples can include an ortho-isomer, a meta-isomer and a para-isomer, and a para-isomer is preferable in terms of the structure thereof.

For example, in a release agent and a glass surface modifier, Q is present in the linking group Y, thereby exerting the effect of allowing an intermolecular hydrogen bond and/or π-π interaction of Q to act to easily form a unimolecular arrangement of molecules. On the contrary, Q is preferably absent in order to enhance dispersion of a fluorine-containing group in a polymer, and therefore proper Q is needed to be selected depending on the intended use.

When Q is present, formation can be easily made according to a conventionally known technique. For example, in the case of a urethane bond ($—OCONH—$), formation can be made by a reaction of a compound having an isocyanate group at 0.9 to 1.1 times relative to a fluorine-containing alcohol derivative in no solvent or an organic solvent such as dichloromethane or tetrahydrofuran at 1 to 10 times by weight by use of 0.1 to 5 mol % of di-n-butyltin dilaurate or the like as a catalyst at 0° C. to 50° C.

When the surface modification group Z is a free phosphonyl group (—P(=O)(OH)$_2$) or a phosphoric acid group (—OP(=O)(OH)$_2$), or an ester or salt thereof, the surface of a metal can be modified and use as a release material of a mold or the like can be made.

Z can also represent a polymerizable group. When Z represents a polymerizable group, the surface of a resin, a film and the like can be modified. In this case, the polymerizable group is also not particularly limited in terms of the type thereof, and may be, for example, a vinyl group, an allyl group, a styryl group, a methacryloyl group or an acryloyl group.

Furthermore, Z can also represent $SiL_kL'_{(3-k)}$.

Here, in the formula: $SiL_kL'_{(3-k)}$, preferably, L represents a hydrolyzable group or a hydroxyl group, L' represents a hydrocarbon group having 1 to 6 carbon atoms, and k represents an integer of 1 to 3. Here, when a plurality of L and L' groups are present, the L and L' groups may be different from or the same as each other.

When Z represents $SiL_kL'_{(3-k)}$, the surfaces of glass, a resin having a hydroxyl group, ceramics, a metal (oxide), and the like can be modified.

When L represents a hydrolyzable group, examples include Cl and $OR^5$ wherein $R^5$ represents an alkyl group having 1 to 6 carbon atoms.

As described in International Publication No. WO 2015/136913, a hydrosilane compound having Si—H can also be used as a bonding group.

The modification method in the case of Z representing $SiL_kL'_{(3-k)}$ can be achieved by a conventional technique in the art.

L' represents a hydrocarbon group having 1 to 6 carbon atoms, and examples include methyl, ethyl, propyl, vinyl and allyl groups.

When a plurality of L and L' groups are present, the L and L' groups may be different from or the same as each other.

The compound described in the present invention can be used to thereby impart water-repellent and oil-repellent properties to the surface of a material, and can be used as a surface modifier.

As the solvent that can be applied to production of the fluorine-containing compound represented by each of the general formulas (1), (2) and (5) of the present invention, any solvent, for example, (halogenated) hydrocarbon-based solvents such as hexane, toluene and dichloromethane, and ether-based solvents such as diethyl ether and tetrahydrofuran can be used as long as such a solvent is inert to the reaction. Such a solvent can be appropriately selected and used depending on the compound for use as the surface modifier, and no solvent may also be used when a material subjected to the reaction is a liquid.

The post-treatment after production of the fluorine-containing compound represented by each of the general formulas (1), (2) and (5) of the present invention can be performed according to a well-known method, and the fluorine-containing compound as a product of interest represented by each of the general formulas (1), (2) and (5) as well as the surface modifier using the compound can be obtained by, for example, obtaining the product of interest by distillation or the like, or obtaining a crude product by a known method such as neutralization, solvent extraction, drying, filtration, condensation or the like, and purifying the crude product by recrystallization, column chromatography or the like.

While the fluorine-containing compound represented by each of the general formulas (1), (2) and (5) of the invention can be used in a modifier as it is, the fluorine-containing compound can also be used with being mixed with other material. For example, such a fluorine-containing compound can be used with being dissolved in an organic solvent.

The organic solvent may be a solvent that does not react with such a fluorine-containing compound, for example, alcohols such as methanol, ethanol and isopropyl alcohol, ketones such as acetone, methyl ethyl ketone and methyl isobutyl ketone, ethers such as tetrahydrofuran, diethyl ether and diisopropyl ether, esters such as ethyl acetate and butyl acetate, halogenated hydrocarbons such as dichloromethane and chloroform, hydrocarbons such as toluene, xylene and hexane, and fluorous solvents such as perfluorohexane and hexafluorobenzene. Such solvents can also be used as a mixture.

Modification of the surface of a resin or film in the present invention can be achieved by polymerizing a compound (monomer A) having a polymerizable group described in the present invention and a monomer B having at least one polymerizable group in the molecule in the presence of a polymerization initiator C to provide a fluorine-containing polymer.

Examples of the monomer B include the following compounds ($X_1$) to ($X_9$):

($X_1$) acrylic acid and methacrylic acid, and esters thereof: methyl, ethyl, butyl, isobutyl, t-butyl, propyl, 2-ethylhexyl, hexyl, decyl, lauryl, stearyl, isobornyl, behenyl, β-hydroxyethyl, glycidyl, phenyl, benzyl and 4-cyanophenyl esters;

($X_2$) fatty acid vinyl esters: acetic acid, propionic acid, caprylic acid, lauric acid, stearic acid, behenic acid and the like;

($X_3$) styrene-based compounds: styrene, α-methylstyrene, p-methylstyrene and the like;

($X_4$) halogenated vinyl or vinylidene compounds: vinyl fluoride, vinyl chloride, vinyl bromide, vinylidene fluoride, vinylidene chloride and the like;

($X_5$) aliphatic allyl esters: allyl heptanoate, allyl caprate, allyl caproate and the like;

($X_6$) vinyl alkyl ketones: vinyl methyl ketone, vinyl ethyl ketone and the like;

($X_7$) acrylamides: N-methylacrylamide, N-methylolacrylamide, N-methylolmethacrylamide and the like;

($X_8$) dienes: 2,3-dichloro-1,3-butadiene, isoprene and the like; and ($X_9$) others: ethylene, acrylonitrile, polyethylene glycol (meth)acrylate, polypropylene glycol (meth)acrylate, methoxy polyethylene glycol (meth)acrylate, methoxy polypropylene glycol (meth)acrylate, vinyl alkyl ether, isoprene and the like.

The monomer B is preferably a (meth)acrylic acid ester, in particular, a (meth)acrylic acid alkyl ester. The number of carbon atoms in such an alkyl group is preferably 1 to 30, more preferably 1 to 20.

As the monomer B, not only a non-fluorine monomer, for example, a (meth)acrylic acid ester, but also a halogen monomer (in particular, a chlorine- or fluorine-containing monomer, for example, vinyl chloride, vinylidene fluoride or tetrafluoroethylene) may be used.

The amount of the monomer B to be used is preferably 1 to 1000 parts by weight, more preferably 10 to 100 parts by weight per 100 parts by weight of the monomer A.

As the polymerization initiator C, an azo-based polymerization initiator is preferably used. Examples of the azo-based polymerization initiator include the following compounds ($Y_1$) to ($Y_6$):

($Y_1$) azonitrile compounds:
2,2'-azobisisobutyronitrile, 2,2'-azobis(2-methylbutyronitrile), 2,2'-azobis(2,4-dimethylvaleronitrile), 1,1'-azobis(1-cyclohexanecarbonitrile), 2,2'-azobis(4-methoxy-2,4-dimethylvaleronitrile), 2-(carbamoylazo)isobutyronitrile and the like;

($Y_2$) azoamide compounds:
2,2'-azobis{2-methyl-N-[1,1-bis(hydroxymethyl)-2-hydroxyethyl]propionamide}, 2,2'-azobis{2-methyl-N-[2-(1-hydroxybutyl)]propionamide}, 2,2'-azobis[2-methyl-N-(2-hydroxyethyl)propionamide], 2,2'-azobis[N-(2-propenyl)-2-methylpropionamide], 2,2'-azobis(N-butyl-2-methylpropionamide), 2,2'-azobis(N-cyclohexyl-2-methylpropionamide) and the like;

($Y_3$) cyclic azoamidine compounds:
2,2'-azobis[2-(2-imidazolin-2-yl)propane]dihydrochloride, 2,2'-azobis[2-(2-imidazolin-2-yl)propane]disulfate dihydrate, 2,2'-azobis[2-[1-(2-hydroxyethyl)-2-imidazolin-2-yl]propane]dihydrochloride, 2,2'-azobis[2-(2-imidazolin-2-yl)propane], 2,2'-azobis(1-imino-1-pyrrolidino-2-methylpropane)dihydrochloride and the like;

($Y_4$) azoamidine compounds:
2,2'-azobis(2-methylpropionamidine)dihydrochloride, 2,2'-azobis[N-(2-carboxyethyl)-2-methylpropionamidine] tetrahydrate and the like;

($Y_5$) others:
dimethyl 2,2'-azobisisobutyrate, 4,4'-azobis(4-cyanovaleric acid), 2,2'-azobis(2,4,4-trimethylpentane), 1,1'-azobis(1-acetoxy-1-phenylethane), dimethyl 1,1'-azobis(1-cyclohexanecarboxylate) and 4,4'-azobis(4-cyanopentanoic acid); and ($Y_6$) fluoroalkyl group-containing azo-based polymerization initiators:
4,4'-azobis(2-(perfluoromethyl)ethyl 4-cyanopentanoate), 4,4'-azobis(2-(perfluorobutyl)ethyl 4-cyanopentanoate), 4,4'-azobis(2-(perfluorohexyl)ethyl 4-cyanopentanoate) and the like.

Among the azo-based polymerization initiators, an initiator having a substituent relatively low in polarity is desirable from the viewpoint of the surface energy of a fluorine-containing highly branched polymer to be obtained, and in particular, 2,2'-azobis(2,4-dimethylvaleronitrile), dimethyl 2,2'-azobisisobutyrate or 2,2'-azobis(2,4,4-trimethylpentane) is preferable.

The polymerization initiator C is used in an amount of 0.1 to 200 mol % based on the total molar number of the monomer A and the monomer B, and is preferably used in an amount of 0.5 to 100 mol %, more preferably 0.5 to 50 mol %, most preferably 0.5 to 20 mol %.

The fluorine-containing polymer is obtained by polymerizing the monomer A and the monomer B in the presence of a predetermined amount of the polymerization initiator C, examples of the polymerization method include known methods such as solution polymerization, dispersion polymerization, precipitation polymerization and bulk polymerization, and in particular, solution polymerization or precipitation polymerization is preferable. In particular, the reaction is preferably performed by solution polymerization in an organic solvent from the viewpoint of control of the molecular weight.

Examples of the organic solvent here used include aromatic hydrocarbon-based solvents such as benzene, toluene, xylene, ethyl benzene and tetralin; aliphatic or alicyclic hydrocarbon-based solvents such as n-hexane, n-heptane, mineral spirit and cyclohexane; halogen-based solvents such as methyl chloride, methyl bromide, methyl iodide, methylene dichloride, chloroform, carbon tetrachloride, trichloroethylene, perchloroethylene and o-dichlorobenzene; ester-based or ester ether-based solvents such as ethyl acetate, butyl acetate, methoxy butyl acetate, methyl cellosolve acetate, ethyl cellosolve acetate and propylene glycol monomethyl ether acetate; ether-based solvents such as diethyl ether, tetrahydrofuran, 1,4-dioxane, methyl cellosolve, ethyl cellosolve, butyl cellosolve and propylene glycol monomethyl ether; ketone-based solvents such as acetone, methyl ethyl ketone, methyl isobutyl ketone, di-n-butyl ketone and cyclohexanone; alcohol-based solvents such as methanol, ethanol, n-propanol, isopropanol, n-butanol, isobutanol, tert-butanol, 2-ethylhexylalcohol and benzyl alcohol; amide-based solvents such as N,N-dimethylformamide and N,N-dimethylacetamide; sulfoxide-based solvents such as dimethyl sulfoxide; heterocyclic compound-based solvents such as N-methyl-2-pyrrolidone, and mixed solvents of two or more thereof.

Among them, aromatic hydrocarbon-based solvents, halogen-based solvents, ester-based or ester ether-based solvents, ether-based solvents, ketone-based solvents, alcohol-based solvents, amide-based solvents, sulfoxide-based solvents and the like are preferable, and toluene, xylene, o-dichlorobenzene, butyl acetate, propylene glycol monomethyl ether acetate, propylene glycol monomethyl ether, 1,4-dioxane, methyl cellosolve, 2-butanone, N,N-dimethylformamide, N,N-dimethylacetamide and the like are particularly preferable.

When the polymerization reaction is performed in the presence of the organic solvent, the content of the organic solvent in the entire polymerization reaction product is preferably 1 to 100 parts by mass, further preferably 5 to 50 parts by mass per part by mass of the monomer A.

The polymerization reaction is performed at ordinary pressure, under a pressurized and sealed condition, or under reduced pressure, and is preferably performed at ordinary pressure from the viewpoint of simplicity of an apparatus and an operation. In addition, the reaction is preferably performed under an atmosphere of an inert gas such as $N_2$. The temperature of the polymerization reaction is preferably 50 to 200° C., further preferably 70 to 150° C.

After completion of the polymerization reaction, the resulting fluorine-containing polymer is recovered according to any method and, if necessary, subjected to a post-treatment such as washing. Examples of the method for recovering a polymer from a reaction solution include a method such as reprecipitation.

The weight average molecular weight (hereinafter, abbreviated as Mw) of the resulting fluorine-containing polymer is preferably 1,000 to 200,000, further preferably 2,000 to 100,000, most preferably 5,000 to 60,000 in terms of polystyrene by gel permeation chromatography (GPC).

Preparation of a release agent by use of the phosphonyl group- or phosphoric acid (ester) group-containing compound obtained in the present invention is performed by dilution with water or an organic solvent so as to provide an aqueous solution, an aqueous dispersion liquid or an organic solvent solution having a concentration of about 0.01 to 30% by weight, preferably about 0.05 to 3% by weight.

The organic solvent used is at least one of alcohols such as methanol, ethanol, n-propanol and isopropanol, ketones such as acetone, methyl ethyl ketone and methyl isobutyl ketone, ethers such as diethyl ether, diisopropyl ether, dioxane and tetrahydrofuran, esters such as ethyl acetate and butyl acetate, polyols or ethers thereof, such as ethylene glycol, propylene glycol, diethylene glycol, triethylene glycol, tetraethylene glycol, dipropylene glycol, tripropylene glycol, tetrapropylene glycol, diethylene glycol monomethyl ether, dipropylene glycol monomethyl ether, tripropylene glycol monomethyl ether and glycerin, polyhydric alcohol derivatives such as methyl cellosolve, ethyl cellosolve, methyl carbitol and ethyl carbitol, and halogenated hydrocarbons such as carbon tetrachloride, methylene chloride, trichloroethylene, perchloroethylene, trichloroethane, trichlorofluoromethane, tetrachlorodifluoroethane, trichlorotrifluoroethane and 1,4-bis(trifluoromethyl)benzene.

The organic solvent can also be here used in combination with water.

To the solution of release agent can also be, if necessary, added an amine-based neutralizing agent such as triethylamine, triethanolamine, tris(2-hydroxyethyl)amine and morpholine, various surfactants for improving wettability of the release agent, such as an ionic surfactant and a nonionic surfactant, silicone oil and silicone varnish for further improving releasability and lubricity, and the like. The amine-based neutralizing agent is used in a proportion of about 0.01 to 300% by weight in the total amount of the amine-based neutralizing agent, a phosphonyl group- or phosphoric acid group-containing compound, and water, an organic solvent, or both of them.

The mold can be coated with the release agent solution by any method commonly used, such as coating by dipping, spraying, brush coating, aerosol propelling or an impregnated cloth. Examples of the molding material formed in the mold coated with the release agent include resins such as polyurethane, polycarbonate, an epoxy resin, a phenol resin, a polyimide resin and a vinyl chloride resin, and rubbers such as natural rubber, chloroprene rubber and fluororubber.

Advantageous Effects of the Invention

The present invention can provide a fluorine-containing compound having a different structure from that of a conventional modification material compound and exerting extremely high water-repellent and oil-repellent effects, as well as a surface modifier using the compound.

EXAMPLES

Hereinafter, Examples of the present invention are shown, but the present invention is not intended to be limited by these Examples.

Here, the following instruments were used in analysis.

$^1$H-NMR, $^{19}$F-NMR: AVANCE II 400 manufactured by Bruker Corporation

GC-MS: GCMS-QP2010Plus (Shimadzu Corporation)

Contact angle measurement: VHX-500F (manufactured by Keyence Corporation)

Gel permeation chromatography (GPC):

Apparatus: 8320GPC manufactured by Tosoh Corporation

Column: TSKgel SuperHM-H, SuperHM-M manufactured by Tosoh Corporation

Column temperature: 40° C.

Solvent: tetrahydrofuran

Detector: RI

Spin coater: ACT-300A manufactured by Active Co., Ltd.

Example 1

Synthesis of 3,3,4,4,5,5,6,6,9,9,10,10,11,12,12,13,13,14,14,14-henicosafluorotetradeca-1,7-diene (3)

1-1) 3,3,4,4,5,5,6,6-octafluoro-8-iodo-1-octene (1)

[Formula 1]

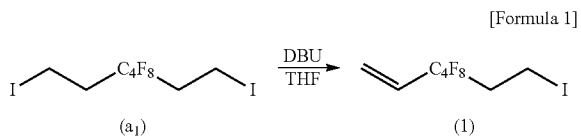

A 100-ml eggplant flask was charged with 150 g (294 mol) of 3,3,4,4,5,5,6,6-octafluoro-1,8-diiodooctane ($\alpha_1$) (reagent of SynQuest Laboratories) and 150 g of THF, and dissolved. After cooling to 5° C. or less, a liquid in which 44.8 g (294 mmol) of diazabicycloundecene was dissolved in 25 g of THF was placed over 1 hour with stirring.

Thereafter, the reaction was conducted at room temperature for 3 hours, thereafter 60 g of water and 120 g of diisopropyl ether were added thereto, and the resultant was separated into two phases. The organic phase was washed with water and saturated saline, and thereafter dried with magnesium sulfate, and the solvent was removed under reduced pressure.

The resulting light yellow slurry was heated and dissolved in hexane and thereafter crystallized by cooling, a crystal precipitated was removed, and the solvent of a filtrate was removed under reduced pressure and thereafter distilled under reduced pressure, to provide 52.9 g of light pink oily compound (1).

The purity and the yield with gas chromatography (GC) were 98.7% and 46.5%, respectively.

$^1$H-NMR (solvent: deuterochloroform, internal standard: tetramethylsilane) δ (ppm): 5.86 (m, 2H, $\underline{CH_2}$=CH—), 5.67 (m, 1H, CH$_2$=$\underline{CH}$—), 3.14 (m, 2H, $\underline{CH_2}$I), 2.61 (m, 2H, CF$_2\underline{CH_2}$CH$_2$I)

$^{19}$F-NMR (solvent: deuterochloroform, internal standard: trifluoromethylbenzene) δ (ppm) −114.44 (s, 2F, CH$_2$=CH—$\underline{CF_2}$), −115.54 (s, 2F, $\underline{CF_2}$CH$_2$CH$_2$I), −123.77 (s, 2F, CF$_2$), −124.06 (s, 4F, CF$_2$)

1-2) 1,1,1,2,2,3,3,4,4,5,5,6,6,9,9,10,10,11,11,12,12-henicosafluoro-8,14-diiodotetradecene (2)

[Formula 2]

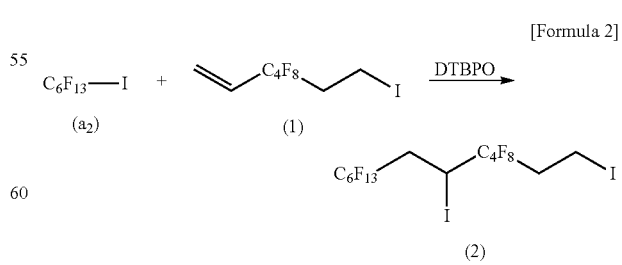

A 150-ml SUS autoclave was charged with 61.3 g (137.4 mmol) of 1-iodoperfluorohexane ($\alpha_2$) (reagent of Tokyo Chemical Industry Co., Ltd.), 50.0 g (130.9 mmol) of 3,3,4,4,5,5,6,6-octafluoro-8-iodo-1-octene (1) and 0.19 g (1.3 mmol) of di-tert-butyl peroxide, the autoclave was sufficiently purged with nitrogen, and thereafter the temperature was raised to conduct the reaction at 120° C. for 2 hours with stirring.

The resulting reaction liquid was subjected to distillation under reduced pressure, to provide 26.7 g of compound (2) being a colorless and transparent liquid as a fraction at 85 to 90° C. (2 kPa).

The purity and the yield with gas chromatography (GC) were 90.5% and 24.7%, respectively.

$^1$H-NMR (solvent: deuterochloroform, internal standard: tetramethylsilane) δ (ppm): 4.56 (m, 1H, CF$_2$CHI), 3.17 (t, 2H, CH$_2$I), 3.04 (m, 2H, CH$_2$CHI), 2.69 (m, 2H, CF$_2$CH$_2$CH$_2$I)

$^{19}$F-NMR (solvent: deuterochloroform, internal standard: trifluoromethylbenzene) δ (ppm): −81.34 (s, 3F, CF$_3$), −109.99 (dd, 2F, CF$_2$CHI), −115.09 (dd, 2F, CF$_2$CH$_2$CHI), −115.43 (s, 2F, CF$_2$CH$_2$CH$_2$I), −117.89 (m, 2F, CH$_2$CF$_2$CF$_2$), −122.27 (s, 2F CF$_2$), −123.2-124.2 (m, 4F, CF$_2$), −126.67 (s, 2F, CF$_3$—CF$_2$)

GC-MS (m/e): 828 (M+)

1-3) 3,3,4,4,5,5,6,6,9,9,10,10,11,12,12,13,13,14,14,14-henicosafluorotetradeca-1,7-diene (3)

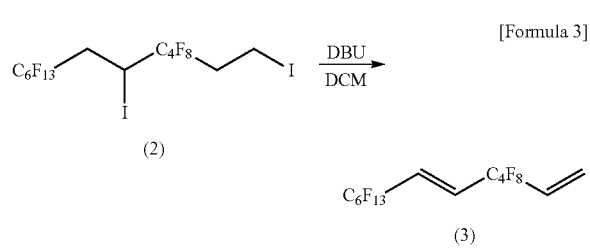

(2)

(3)

In a 200-ml three-necked flask, 43.5 g (52.5 mmol) of compound (2) was dissolved in 100 g of dichloromethane and thereafter cooled under a nitrogen atmosphere, and 17.6 g (115.5 mmol) of diazabicycloundecene was dropped thereto at 5 to 10° C. over 1 hour.

The reaction was conducted at room temperature with stirring overnight, and thereafter 100 g of a 1% by weight hydrochloric acid solution was added to separate an aqueous phase. An organic phase was washed with water, 1% by weight potassium hydrogen carbonate, and saturated saline, thereafter the solvent was removed, and the resultant was treated with silica and then subjected to distillation under reduced pressure, to obtain 19.0 g of compound (3) being a colorless and transparent liquid as a fraction at 90 to 94° C. (2 kPa). The yield was 90.1%.

$^1$H-NMR (solvent: deuterochloroform, internal standard: tetramethylsilane) δ (ppm): 6.43 (m, 2H, —CH═CH—), 5.96 (m, 2H, —CH═CH$_2$), 5.82 (m, 1H, —CH═CH$_2$)

$^{19}$F-NMR (solvent: deuterochloroform, internal standard: trifluoromethylbenzene) δ (ppm): −81.34 (s, 3F, CF$_3$), −112.34 (m, 2F, CF$_2$CH═), −114.48 (m, 2F, CF$_2$CH═), −114.58 (m, 2F, CF$_2$CH═), −122.07 (s, 2F, CF$_2$), −123.32 (s, 2F, CF$_2$), −123.4-123.9 (m, 6F, CF$_2$), −126.64 (s, 2F, CF$_3$—CF$_2$)

MS (m/e): 553 (M−F)

Example 2

Synthesis of 4,4,5,5,6,6,7,7,8,8,9,9,12,12,13,13,14,14,15,15,15-henicosafluoro-10-pentadecen-1-ol (7)

2-1) Synthesis of 1,1,2,2,3,3,4,4,5,5,6,6,9,9,10,10,11,11,12,12,12-henicosafluoro-1,8-diiodododecane (4)

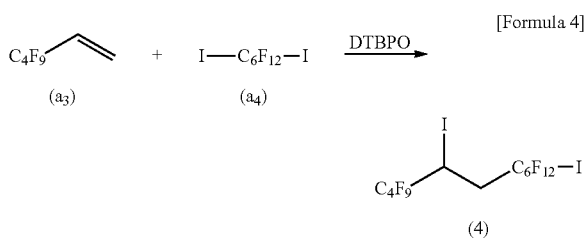

A 150-ml SUS autoclave was charged with 88.42 g (0.36 mol) of 3,3,4,4,5,5,6,6,6-nonafluoro-1-octene (α$_3$) (reagent of Tokyo Chemical Industry Co., Ltd.), 199.00 g (0.36 mol) of 1,1,2,2,3,3,4,4,5,5,6,6-dodecafluoro-1,6-diiodohexane (α$_4$) (produced by Tosoh F-Tech, Inc.) and 0.53 g (0.004 mol) of di-tert-butyl peroxide, and the autoclave was purged with nitrogen.

After sealing, the temperature was raised to conduct the reaction at 120° C. for 3 hours and at 150° C. for 2 hours. After cooling, the resulting reaction liquid was subjected to distillation under reduced pressure, to obtain 85.13 g of compound (4) as a fraction at 111° C. and 0.4 kPa. The yield was 29.2%.

$^1$H-NMR (solvent: deuterochloroform, internal standard: tetramethylsilane) δ (ppm): 4.63 (m, 1H, CF$_2$CHI), 3.16 (m, 1H, CF$_2$CH$_2$)

$^{19}$F-NMR (solvent: deuterochloroform, internal standard: trifluoromethylbenzene) δ (ppm): −59.38 (m, 2F, CF$_2$I), −81.31 (t, 3F, CF$_3$), −105.81 (dd, 2F, CF$_2$CHI), −113.49 (m, 2F, CF$_2$CF$_2$I), −114.95 (m, 2F, CH$_2$CF$_2$), −119.27 (m, 2F, CH$_2$CF$_2$), −121.46 (m, 2F, CF$_2$), −122.00 (m, 2F, CF$_2$), −124.13 (s, 2F, CF$_2$), −126.31 (m, 2F, CF$_2$)

2-2) Synthesis of 1,1,2,2,3,3,4,4,5,5,6,6,9,9,10,10,11,11,12,12,12-henicosafluorol-iodo-7-dodecene (5)

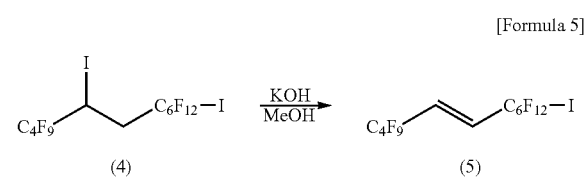

A 100-ml two-necked flask was charged with 41.45 g of a 10% potassium hydroxide-methanol solution, and 80.00 g (116.63 mmol) of compound (4) was dropped at room temperature over 40 minutes. After the reaction at room temperature for 1.5 hours, the reaction liquid was washed with 35 g of water, and the organic layer was diluted with dichloromethane. Furthermore, the organic layer was washed with 35 g of 1% hydrochloric acid, 40 g of water and 40 g of saturated saline, and thereafter the water content was removed from the organic phase by anhydrous sodium sulfate to obtain 63.94 g of compound (5). The yield was 53.9%.

$^1$H-NMR (solvent: deuterochloroform, internal standard: tetramethylsilane) δ (ppm): 6.48 (m, 2H, C$_4$F$_9$C$\underline{H}$=C$\underline{H}$C$_6$F$_{12}$)

$^{19}$F-NMR (solvent: deuterochloroform, internal standard: trifluoromethylbenzene) δ (ppm): −59.38 (m, 2F, C$\underline{F}_2$I), −81.60 (t, 3F, CF$_3$), −113.47 (m, 2F, C$\underline{F}_2$CF$_2$I), −114.42 (m, 2F, C$\underline{F}_2$CH), −114.67 (m, 2F, CHC$\underline{F}_2$), −121.49 (m, 2F, CF$_2$), −121.86 (m, 2F, CF$_2$), −123.77 (m, 2F, CF$_2$), −124.78 (m, 2F, CF$_2$), −126.31 (m, 2F, CF$_2$)

2-3) Synthesis of 4,4,5,5,6,6,7,7,8,8,9,9,12,12,13,13,14,14,15,15,15-henicosafluoro-10-pentadecen-1-ol (6)

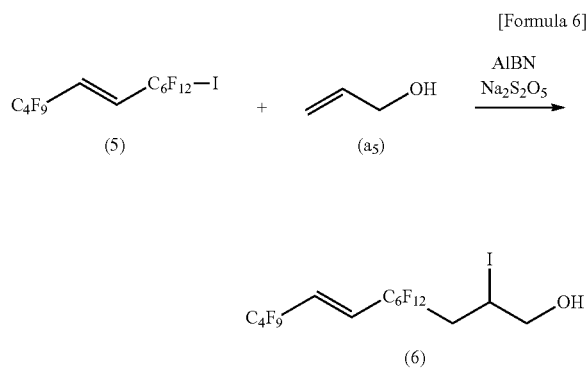

[Formula 6]

A 100-ml eggplant flask was charged with 10.00 g (14.45 mmol) of compound (5) and 7.7 g of an aqueous 25% by weight sodium disulfite solution, and the flask was sufficiently purged with nitrogen. The inner temperature was raised to 70° C., and a solution in which 0.05 g (0.30 mmol) of azobisisobutyronitrile was dissolved in 1.01 g (17.34 mmol) of allyl alcohol (a$_5$) was slowly dropped under vigorous stirring over 1 hour with the inner temperature being kept at 75 to 85° C. After the dropping, the reaction was performed at 75° C. for 16 hours, and thereafter the resultant was treated at 100° C. for 10 minutes.

After cooling, the resultant was subjected to extraction with 15 g of dichloromethane and separated into two phases, and thereafter the organic phase was washed with 15 g of water and 20 g of saturated saline, and thereafter dried with magnesium sulfate. The organic phase was condensed under reduced pressure to obtain 9.96 g of compound (6). The yield was 89.4%.

$^1$H-NMR (solvent: deuterochloroform, internal standard: tetramethylsilane) δ (ppm): 6.47 (m, 2H, C$_4$F$_9$C$\underline{H}$=C$\underline{H}$C$_6$F$_{12}$), 4.40 (m, 1H, C$\underline{H}$I), 3.77 (m, 2H, C$\underline{H}_2$O), 2.88 (m, 2H, C$\underline{H}_2$CF$_2$), 1.99 (s, 1H, OH)

$^{19}$F-NMR (solvent: deuterochloroform, internal standard: trifluoromethylbenzene) δ (ppm): −81.58 (t, 3F, CF$_3$), −113.93 (m, 2F, C$\underline{F}_2$CH$_2$), −114.42 (m, 2F, C$\underline{F}_2$CH), −122.00 (m, 4F, CF$_2$CF$_2$), −123.98 (m, 4F, CF$_2$CF$_2$), −124.82 (m, 2F, CF$_2$), −126.33 (m, 2F, CF$_2$)

2-4) Synthesis of 4,4,5,5,6,6,7,7,8,8,9,9,12,12,13,13,14,14,15,15,15-henicosafluoro-10-pentadecen-1-ol (7)

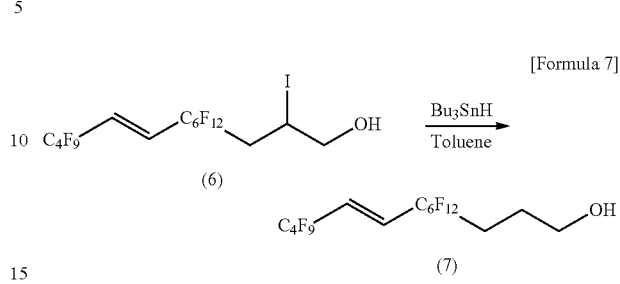

[Formula 7]

A 50-ml two-necked flask was charged with 0.34 g (1.95 mmol) of azobisisobutyronitrile, 9.50 g (13.01 mmol) of compound (6) and 5.98 g (19.52 mmol) of tributyltin hydride, and the reaction was conducted at 70° C. for 3 hours. The reaction liquid was diluted with 40 g of diisopropyl ether, washed with 50 g of water, 50 g of an aqueous 1 M potassium fluoride solution and 50 g of saturated saline, and thereafter dried with anhydrous magnesium sulfate. The organic layer was condensed under reduced pressure and thereafter recrystallized in hexane to obtain 4.45 g of compound (7). The yield was 54.0%.

$^1$H-NMR (solvent: deuterochloroform, internal standard: tetramethylsilane) δ (ppm): 6.47 (m, 2H, C$_4$F$_9$C$\underline{H}$=C$\underline{H}$C$_6$F$_{12}$), 3.70 (m, 2H, C$\underline{H}_2$O), 2.22 (m, 2H, C$\underline{H}_2$CF$_2$), 1.85 (m, 2H, CH$_2$), 1.49 (s, 1H, OH)

$^{19}$F-NMR (solvent: deuterochloroform, internal standard: trifluoromethylbenzene) δ (ppm): −81.59 (t, 3F, CF$_3$), −114.53 (m, 4F, C$\underline{F}_2$CH), −114.85 (m, 2F, C$\underline{F}_2$CH$_2$), −122.17 (m, 4F, CF$_2$CF$_2$), −123.97 (m, 4F, CF$_2$CF$_2$), −124.78 (m, 2F, CF$_2$), −126.33 (m, 2F, CF$_2$)

Example 3

Synthesis of 4,4,5,5,6,6,7,7,8,8,9,9,12,12,13,13,14,14,15,15,16,16,17,17,17-pentacosafluoro-10-heptadecen-1-ol (11)

3-1) Synthesis of 1,1,2,2,3,3,4,4,5,5,6,6,9,9,10,10,11,11,12,12,13,13,14,14,14-pentacosafluoro-1,8-diiodotetradecane (8)

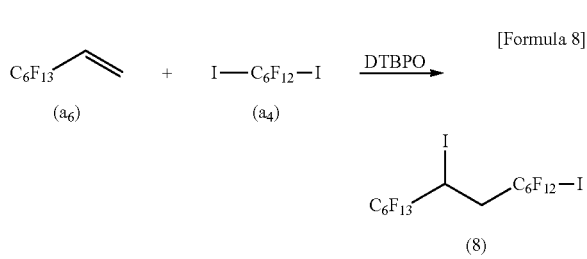

[Formula 8]

A 150-ml SUS autoclave was charged with 31.24 g (0.090 mol) of 3,3,4,4,5,5,6,6,7,7,8,8,8-nonafluoro-1-decene (α$_6$) (reagent of Tokyo Chemical Industry Co., Ltd.), and 50.00 g (0.090 mol) of 1,1,2,2,3,3,4,4,5,5,6,6-dodecafluoro-1,6-diiodohexane (α$_4$) (produced by Tosoh F-Tech, Inc.) and 0.13 g (0.001 mol) of di-tert-butyl peroxide, and the autoclave was purged with nitrogen.

After sealing, the temperature was raised to conduct the reaction at 120° C. for 3 hours and at 150° C. for 2 hours. After cooling, the resulting reaction liquid was condensed under reduced pressure to provide 65.21 g of a crude product of compound (8). The purity with gas chromatography (GC) was 48.5%.

3-2) Synthesis of 1,1,2,2,3,3,4,4,5,5,6,6,9,9,10,10, 11,11,12,12,13,13,14,14,14-pentacosafluoro-1-iodo-7-tetradecene (9)

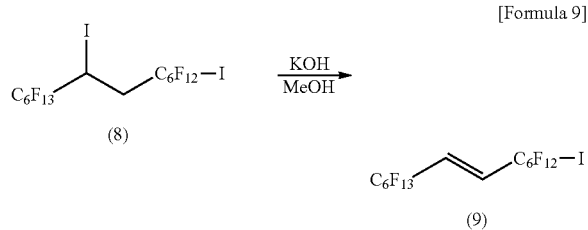

[Formula 9]

A 100-ml two-necked flask was charged with 65.21 g of a mixture including (8) obtained in the reaction, and 55.71 g of a 10% potassium hydroxide-methanol solution was dropped under room temperature over 15 minutes. After the reaction at room temperature for 1 hour, the reaction liquid was washed with 50 g of water, 50 g of an aqueous 10% ammonium chloride solution and 50 g of saturated saline. The organic layer was diluted with dichloromethane. Furthermore, the organic layer was washed with g of 1% hydrochloric acid, 40 g of water and 40 g of saturated saline. The resulting organic layer was subjected to distillation under reduced pressure, to obtain 21.69 g of compound (9) as a fraction at 108° C. and 0.8 kPa. The yield was 31.1%.

$^1$H-NMR (solvent: deuterochloroform, internal standard: tetramethylsilane) δ (ppm): 6.46 (m, 2H, $C_4F_9$ C$\underline{H}$=C$\underline{H}C_6F_{12}$)

$^{19}$F-NMR (solvent: deuterochloroform, internal standard: trifluoromethylbenzene) δ (ppm): −59.43 (m, 2F, C$\underline{F_2}$I), −81.44 (t, 3F, $CF_3$), −113.49 (m, 2F, C$\underline{F_2}CF_2$I), −114.42 (m, 4F, C$\underline{F_2}$CH), −121.46 (m, 2F, $CF_2$), −121.84 (m, 2F, $CF_2$), −122.09 (m, 2F, $CF_2$), −123.35 (m, 2F, $CF_2$), −123.84 (m, 4F, $CF_2CF_2$), −126.73 (m, 2F, $CF_2CF_3$)

3-3) Synthesis of 4,4,5,5,6,6,7,7,8,8,9,9,12,12,13,13, 14,14,15,15,16,16,17,17,17-pentacosafluoro-2-iodo-10-heptadecen-1-ol (10)

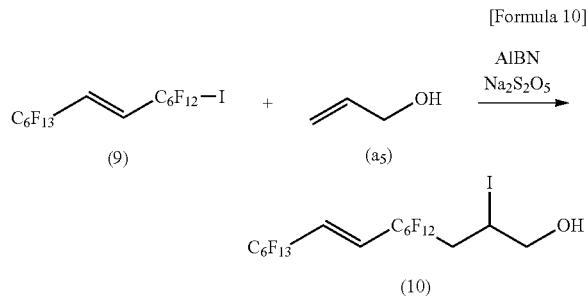

[Formula 10]

A 100-ml eggplant flask was charged with 10.00 g (12.95 mmol) of compound (9) and 6.9 g of an aqueous 25% by weight sodium disulfite solution, and the flask was sufficiently purged with nitrogen. The inner temperature was raised to 70° C., and a solution in which 0.04 g (0.27 mmol) of azobisisobutyronitrile was dissolved in 0.90 g (15.54 mmol) of allyl alcohol ($α_5$) was slowly dropped under vigorous stirring over 1 hour with the inner temperature being kept at 75 to 85° C. After the dropping, the reaction was performed with stirring at 75° C. for 16 hours, and thereafter the resultant was treated at 100° C. for 10 minutes.

After cooling, the resultant was subjected to extraction with 50 g of dichloromethane and separated into two phases, and thereafter the organic phase was washed with 20 g of water and 20 g of saturated saline, and thereafter dried with magnesium sulfate. The organic phase was condensed under reduced pressure to obtain 9.68 g of compound (10). The yield was 90.0%.

$^1$H-NMR (solvent: deuterochloroform, internal standard: tetramethylsilane) δ (ppm): 6.49 (m, 2H, $C_4F_9$ C$\underline{H}$=C$\underline{H}C_6F_{12}$), 4.43 (m, 1H, C$\underline{H}$I), 3.79 (m, 2H, C$\underline{H_2}$O), 2.92 (m, 2H, C$\underline{H_2}CF_2$), 1.99 (s, 1H, OH)

$^{19}$F-NMR (solvent: deuterochloroform, internal standard: trifluoromethylbenzene) δ (ppm): −81.32 (t, 3F, $CF_3$), −113.96 (m, 2F, C$\underline{F_2}CH_2$), −114.38 (m, 4F, C$\underline{F_2}$CH), −122.17 (m, 6F, $CF_2CF_2CF_2$), −123.38 (m, 2F, $CF_2$), −123.89 (m, 4F, $CF_2CF_2$), −124.09 (m, 2F, $CF_2$), −126.67 (m, 2F, $CF_2$)

3-4) Synthesis of 4,4,5,5,6,6,7,7,8,8,9,9,12,12,13,13, 14,14,15,15,16,16,17,17,17-pentacosafluoro-10-heptadecen-1-ol (11)

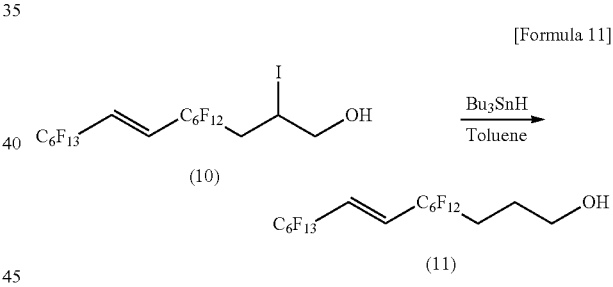

[Formula 11]

A 50-ml two-necked flask was charged with 0.15 g (0.90 mmol) of azobisisobutyronitrile, 5.00 g (6.02 mmol) of compound (10), 2.63 g (9.03 mmol) of tributyltin hydride and 10 g of toluene, and the reaction was conducted at 70° C. for 3 hours. The reaction liquid was diluted with 40 g of diisopropyl ether, washed with 40 g of water, 40 g of an aqueous 1 M potassium fluoride solution and 40 g of saturated saline, and thereafter dried with anhydrous magnesium sulfate. The organic layer was condensed under reduced pressure and thereafter recrystallized in hexane to obtain 3.48 g of compound (11). The yield was 75.2%.

$^1$H-NMR (solvent: deuterochloroform, internal standard: tetramethylsilane) δ (ppm): 6.48 (m, 2H, $C_4F_9$ C$\underline{H}$=C$\underline{H}C_6F_{12}$), 3.71 (m, 2H, C$\underline{H_2}$O), 2.20 (m, 2H, C$\underline{H_2}CF_2$), 1.86 (m, 2H, $CH_2$), 1.70 (s, 1H, OH)

$^{19}$F-NMR (solvent: deuterochloroform, internal standard: trifluoromethylbenzene) δ (ppm): −81.36 (t, 3F, $CF_3$), −114.39 (m, 4F, C$\underline{F_2}$CH), −114.86 (m, 2F, C$\underline{F_2}CH_2$), −122.13 (m, 6F, $CF_2CF_2CF_2$), −123.39 (m, 2F, $CF_2$), −123.96 (m, 6F, $CF_2CF_2CF_2$), −126.69 (m, 2F, $CF_2$)

Example 4

Synthesis of 4,4,5,5,6,6,7,7,10,11,11,12,12,13,13,14,14,15,15,15-eicosafluoro-9-pentadecen-1-ol (16)

4-1) Synthesis of 1,1,2,2,3,3,4,4,7,7,8,8,9,9,10,10,11,11,12,12,12-henicosafluoro-1,6-diiodododecane (12)

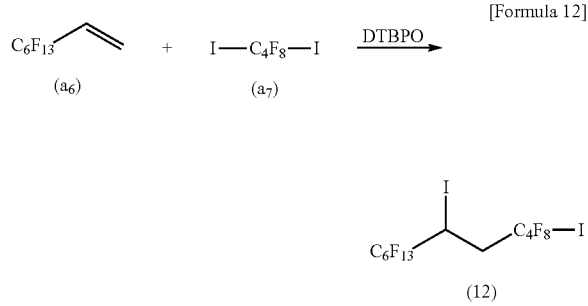

[Formula 12]

A 150-ml SUS autoclave was charged with 76 g (0.22 mol) of 3,3,4,4,5,5,6,6,7,7,8,8,8-tridecafluoro-1-octene ($α_6$) (reagent of Tokyo Chemical Industry Co., Ltd.), and 200 g (0.44 mol) of 1,1,2,2,3,3,4,4-octafluoro-1,4-diiodobutane ($α_7$) (produced by Tosoh F-Tech, Inc.) and 0.65 g (0.004 mol) of di-tert-butyl peroxide, and the autoclave was purged with nitrogen.

After sealing, the temperature was raised to conduct the reaction at 120° C. for 3 hours and at 150° C. for 2 hours. After cooling, the resulting reaction liquid was subjected to distillation under reduced pressure, to obtain 94.58 g of compound (12) as a fraction at 130 to 135° C. and 0.4 kPa. The yield was 53.9%.

$^1$H-NMR (solvent: deuterochloroform, internal standard: tetramethylsilane) δ (ppm): 4.55 (m, 1H, CF$_2$CHI), 2.97 (m, 1H, CF$_2$CH$_2$)

$^{19}$F-NMR (solvent: deuterochloroform, internal standard: trifluoromethylbenzene) δ (ppm): −59.33 (s, 2F, CF$_2$I), −81.30 (s, 3F, CF$_3$), −105.54 (dd, 2F, CF$_2$CHI), −112.98 (m, 2F, CF$_2$CF$_2$CHI), −114.99 (m, 2F, CH$_2$CF$_2$), −117.92 (m, 2F, CH$_2$CF$_2$CF$_2$), −122.16 (s, 2F, CF$_2$), −123.23-123.25 (m, 4F, CF$_2$x2), −126.61 (s, 2F, CF$_3$—CF$_2$)

MS (m/e): 800 (M+)

4-2) Synthesis of 4,4,5,5,6,6,7,7,10,10,11,11,12,12,13,13,14,14,15,15,15-henicosafluoro-2,9-diiodo-1-pentadecanol (13)

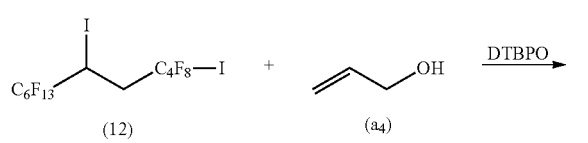

[Formula 13]

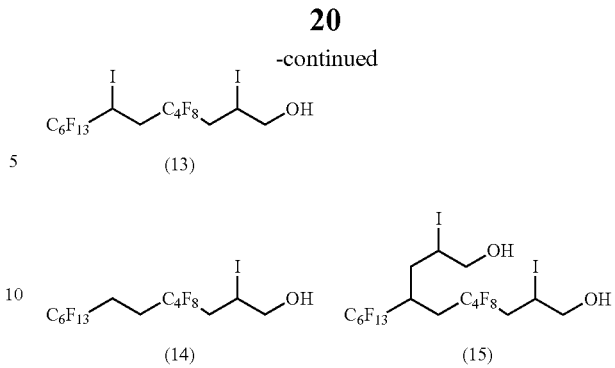

A 100-ml eggplant flask was charged with 27.75 g (34.7 mmol) of compound (12) and 18.5 g of an aqueous 25% by weight sodium disulfite solution, and the flask was sufficiently purged with nitrogen.

The inner temperature was raised to 70° C., and a solution in which 0.12 g (0.73 mmol) of azobisisobutyronitrile was dissolved in 4.03 g (69.4 mmol) of allyl alcohol ($α_5$) was slowly dropped under vigorous stirring over 2 hours with the inner temperature being kept at 75 to 85° C. After the dropping, the reaction was performed with stirring at 75° C. for 16 hours, and thereafter the resultant was treated at 100° C. for 10 minutes.

After cooling, the resultant was subjected to extraction with 23 g of dichloromethane and separated into two phases, and thereafter the organic phase was washed with 38 g of water and 40 g of saturated saline, and thereafter dried with magnesium sulfate. The organic phase was condensed under reduced pressure to obtain a brown crude product of compound (13).

The purity and the yield with gas chromatography (GC) were 31.9% and 24.7%, respectively.

The crude product included 19.3% of raw material (12), 17.2% of reduced product (14) with one iodine and 10.6% of 2-adduct (15). Each calculation was made depending on the area percentage by GC.

4-3) Synthesis of 4,4,5,5,6,6,7,7,10,11,11,12,12,13,13,14,14,15,15,15-eicosafluoro-9-pentadecen-1-ol (16)

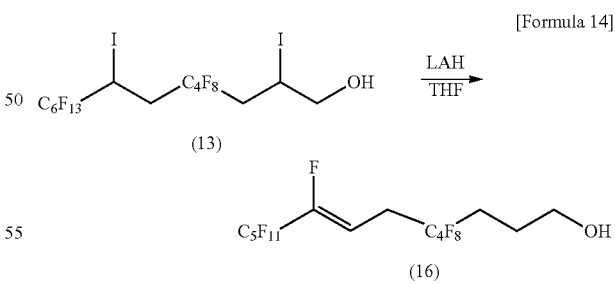

[Formula 14]

To a 100-ml four-necked flask whose content was purged with nitrogen were added 1.27 g (33.51 mmol) of lithium aluminum hydride and 43.68 g of tetrahydrofuran, and cooled to −10° C. or less, and a solution in which 5.66 g of a mixture including (13) obtained in the reaction was dissolved in 21.6 g of tetrahydrofuran was dropped at −10° C. over 1 hour.

After the above reaction, the reaction was conducted with stirring at room temperature overnight. The reaction liquid was slowly added to 300 g of an aqueous saturated ammonium chloride solution with careful attention to foaming. Thereafter, filtration was made, a crystal was rinsed with 300 ml of ethyl acetate, and the resulting filtrate was separated into two phases. The organic phase was washed with 220 g of 2.5% saline and 150 g of saturated saline, thereafter the water content was removed from the organic phase by anhydrous sodium sulfate, and thereafter the solvent was distilled off under reduced pressure.

The resulting orange oily product was purified and separated by a silica column chromatographic method (filler: silica gel 60N produced by Kanto Kagaku, eluent: dichloromethane) to obtain 0.32 g of compound (20). The yield from compound (12) was 1.5%.

$^1$H-NMR (solvent: deuterochloroform, internal standard: tetramethylsilane) δ (ppm): 5.66 (dt, 1H, CF=CH—), 3.66 (t, 2H, CH$_2$OH), 3.01 (td, 2H, CF$_2$CH$_2$CH=), 2.10 (tt, 2H, CF$_2$CH$_2$CH$_2$), 1.78 (m, 2H, CH$_2$CH$_2$CH$_2$), 1.66 (s, 1H, —OH)

$^{19}$F-NMR (solvent: deuterochloroform, internal standard: trifluoromethylbenzene) δ (ppm): −81.33 (t, 3F, CF$_3$), −113.06 (s, 2F, CF$_2$—CF=), −114.95 (m, 2F, CF$_2$), −118.49 (m, 2F, CH$_2$CF$_2$CF$_2$), −123.43 (s, 2F, CF$_2$), −123.7-124.2 (m, 6F, CF$_2$x3), −125.42 (s, 1F, —CF=CH), −126.62 (s, 2F, CF$_3$—CF$_2$)

GC-MS (m/e): 800 (M+)

Example 5

Synthesis of 3,3,4,4,5,5,6,6,7,7,8,11,11,12,12,13,13, 14,14,15,15,16,16,16-tetracosafluoro-8-hexadecen-1-ol (18)

5-1) Synthesis of 3,3,4,4,5,5,6,6,7,7,8,11,11,12,12, 13,13,14,14,15,15,16,16,16-tetracosafluorohexa-decyl-1,8-diene (17)

[Formula 15]

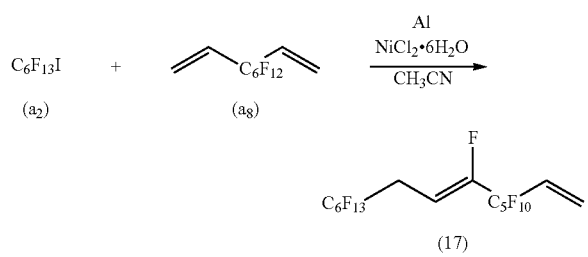

A 500-ml three-necked flask was charged with 6.09 g (225.90 mol) of an aluminum powder (reagent of Wako Pure Chemical Industries, Ltd.), 5.37 g (22.59 mmol) of nickel chloride hexahydrate (reagent of Wako Pure Chemical Industries, Ltd.), 177 g of acetonitrile and 40.00 g (113.0 mmol) of 3,3,4,4,5,5,6,6,7,7,8,8-dodecafluorooctadecyl-1, 9-diene (α$_8$) (produced by Tosoh F-Tech, Inc.), and 50.37 g (446.0 mol) of 1-iodo-1,1,2,2,3,3,4,4,5,5,6,6,6-tridecafluorohexane (α$_2$) was dropped under room temperature over 15 minutes. After the reaction at room temperature for 12 hours, 100 g of 2.5% hydrochloric acid was added to the reaction liquid, and the resultant was subjected to extraction with 100 g of diisopropyl ether three times. The resulting organic layer was washed with 200 g of an aqueous 5% sodium hydrogen carbonate solution and 200 g of saturated saline, and thereafter dried with anhydrous magnesium sulfate. The organic layer was condensed under reduced pressure and thereafter distillated under reduced pressure to obtain 19.21 g of compound (17) as a fraction at 168 to 170° C. and 0.4 kPa. The yield was 25.8%.

$^1$H-NMR (solvent: deuterochloroform, internal standard: tetramethylsilane) δ (ppm): 5.92 (m, 2H, CH=CH$_2$) 5.73 (m, 1H, CH=CH$_2$) 5.67 (m, 1H, CH$_2$CHCF) 3.03 (m, 2H, CH$_2$CHCF)

$^{19}$F-NMR (solvent: deuterochloroform, internal standard: trifluoromethylbenzene) δ (ppm): −81.43 (t, 3F, CF$_3$), −112.96 (m, 2F, CF$_2$CH), −114.38 (m, 2F, CF$_2$CH$_2$), −118.47 (m, 2F, CF$_2$), −121.99 (m, 4F, CF$_2$CF$_2$), −123.50 (m, 6F, CF$_2$CF$_2$CF$_2$), −124.20 (m, 2F, CF$_2$), −124.59 (m, 1F, CF), −126.66 (m, 2F, CF$_2$)

5-2) Synthesis of 3,3,4,4,5,5,6,6,7,7,8,11,11,12,12, 13,13,14,14,15,15,16,16,16-tetracosafluoro-8-hexadecen-1-ol (18)

[Formula 16]

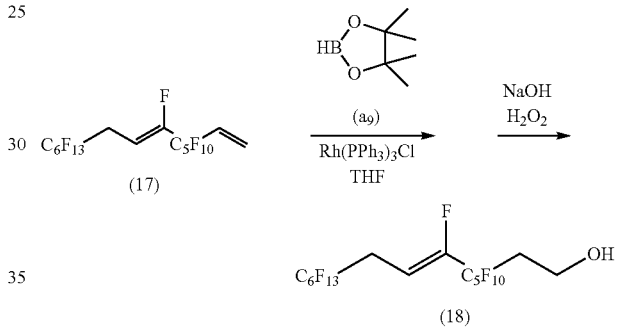

A 100-ml three-necked flask was charged with 0.28 g (0.31 mmol) of tris(triphenylphosphine)rhodium (I) chloride (reagent of Tokyo Chemical Industry Co., Ltd.), 20 g of tetrahydrofuran and 2.30 g (16.8 mmol) of 4,4,5,5-tetramethyl-1,3,2-dioxaborolane (α$_9$) (reagent of Tokyo Chemical Industry Co., Ltd.), and the resulting mixture was stirred under room temperature for 5 minutes. 10.00 g (15.3 mmol) of compound (17) was added thereto, and the reaction was conducted at room temperature for 24 hours, and thereafter 30 g of an aqueous 3 M sodium hydroxide solution was added to the reaction liquid, and g of an aqueous 30% hydrogen peroxide solution was dropped over 5 minutes. After 150 g of an aqueous saturated ammonium chloride solution was added, the resultant was subjected to extraction with 150 g of diisopropyl ether twice. The resulting organic layer was washed with 150 g of saturated saline, and thereafter dried with anhydrous magnesium sulfate. The organic layer was condensed under reduced pressure and thereafter the resulting brown oily product was purified and separated by silica gel column chromatography (filler: silica gel C-300 produced by Wako Pure Chemical Industries Co., Ltd., eluent: ethyl acetate/hexane=1:2) to obtain 3.00 g of compound (18).

The yield was 29.2%.

$^1$H-NMR (solvent: deuterochloroform, internal standard: tetramethylsilane) δ (ppm): 5.68 (m, 1H, CH=CH$_2$), 3.94 (t, 2H, CF$_2$CH$_2$CH$_2$OH), 3.04 (m, 2H, CH$_2$CHCF), 2.35 (m, 2H, CF$_2$CH$_2$CH$_2$OH) 2.01 (s, 1H, OH)

$^{19}$F-NMR (solvent: deuterochloroform, internal standard: trifluoromethylbenzene) δ (ppm): −81.41 (t, 3F, CF$_3$), −112.91 (m, 2F, CF$_2$CH), −113.97 (m, 2F, CF$_2$CH$_2$), −118.45 (m, 2F, CF$_2$), −122.30 (m, 4F, CF$_2$CF$_2$), −123.47 (m, 6F, CF$_2$CF$_2$CF$_2$), −124.34 (m, 2F, CF$_2$), −124.34 (m, 1F, CF), −126.66 (m, 2F, CF$_2$)

Example 6

Synthesis of 3,3,4,4,5,5,6,6,7,7,8,11,12,12,13,13,14,14,15,15,16,16,16-tricosafluoro-1,8,10-hexadeca-triene (19)

[Formula 17]

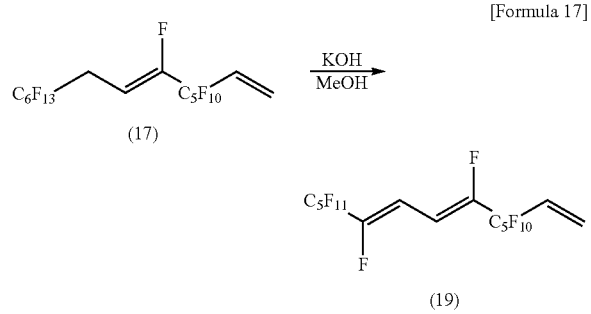

A 10-ml vial was charged with 5.00 g of compound (17), and 4.67 g of a 10% potassium hydroxide-methanol solution was dropped under room temperature over 5 minutes. After the reaction at room temperature for 1 hour, the reaction liquid was washed with 5 g of an aqueous 10% ammonium chloride solution, 5 g of water and 5 g of saturated saline. The resulting organic layer was condensed under reduced pressure to obtain 4.46 g of compound (19). The yield was 93.9%.

$^1$H-NMR (solvent: deuterochloroform, internal standard: tetramethylsilane) δ (ppm): 6.46 (m, 2H, CFCH═CHCF), 5.93 (m, 2H, CH═CH$_2$), 5.75 (m, 1H, CH═CH$_2$)

19F-NMR (solvent: deuterochloroform, internal standard: trifluoromethylbenzene) δ (ppm): −81.38 (m, 3F, CF$_3$), −114.34 (m, 2F, CF$_2$CH), −118.46 (m, 4F, CF$_2$CF), −119.67 (m, 1F, CF), −120.56 (m, 1F, CF), −121.92 (m, 2F, CF$_2$), −123.30 (m, 6F, CF$_2$CF$_2$CF$_2$), −124.17 (m, 2F, CF$_2$), −126.66 (m, 2F, CF$_2$)

Example 7

Synthesis of 3,3,4,4,5,5,6,6,7,7,8,11,12,12,13,13,14,14,15,15,16,16,16-tricosafluoro-8,10-hexadecadien-1-ol (20)

[Formula 18]

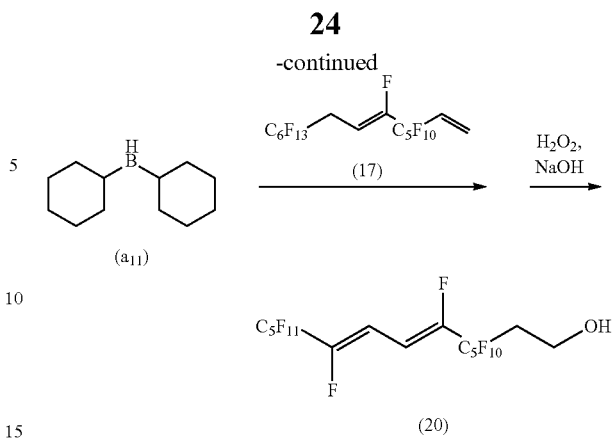

A 200-ml three-necked flask which was purged with nitrogen was charged with 1.72 g (22.6 mmol) of a borane dimethyl sulfide complex and 47.9 g of tetrahydrofuran, and cooled to −15° C.

Under a nitrogen atmosphere, 3.72 g (45.3 mmol) of cyclohexene (α$_{10}$) was dropped at −15° C. or less over 30 minutes with stirring by a magnetic stirrer. After the dropping, the resultant was stirred at 0° C. for 2 hours and thereafter a solution in which 10 g (15.29 mmol) of compound (17) was dissolved in 30 g of tetrahydrofuran was dropped at 5° C. or less over 60 minutes.

Thereafter, the reaction was conducted with stirring at 5° C. for 3 hours and at room temperature for 63 hours. After cooling to 0° C. again, 15.29 g (76.4 mmol) of an aqueous 20% by weight sodium hydroxide solution was dropped over 10 minutes, 17.33 g (152.9 mmol) of a 30% by weight hydrogen peroxide solution was subsequently dropped over 30 minutes, and thereafter the reaction was performed with stirring at room temperature for 2 hours.

After 27.56 g of 10% by weight hydrochloric acid was dropped to the reaction liquid over 30 minutes, 30 g of diisopropyl ether was added to perform extraction, and thereafter the organic phase was washed with 30 g of water once and 30 g of saturated saline twice. The organic phase was dehydrated by anhydrous magnesium sulfate and thereafter the solvent was distilled off under reduced pressure to provide 9.89 g of a light yellow oily product.

The resulting crude product was subjected to removal of cyclohexanol by Kugelrohr distillation and thereafter purified by silica gel column chromatography (eluent: ethyl acetate) to obtain 1.30 g of compound (20).

The resulting compound (20) was analyzed, and the following results were obtained.

The purity with gas chromatography (GC) was 89.3%. The yield was 11.8%.

$^1$H-NMR (solvent: deuterochloroform, internal standard: tetramethylsilane) δ (ppm): 6.63 (dt, 2H, —CF═CHCH═CF—), 3.74 (t, 2H, CH$_2$O), 3.28 (b, 1H, —OH), 2.28 (tt, CF$_2$CH$_2$)

$^{19}$F-NMR (solvent: deuterochloroform, internal standard: trifluoromethylbenzene) δ (ppm): −81.69 (t, 3F, CF$_3$), −114.03 (m, 2F, CF$_2$CH$_2$), −118.47 (m, 4F, CF$_2$), −121.09 (m, 1F, CF═CH), −21.88 (m, 1F, CF═CH), −122.31 (m, 2F CF$_2$), −123.42 (m, 2F, CF$_2$), −123.55 (m, 2F CF$_2$), −124.42 (m, 4F CF$_2$x2), −126.82 (m, 2F, CF$_2$)

GC-MS (m/e): 652 (M+)

Example 8

Synthesis of 1-trichlorosilyl-3,3,4,4,5,5,6,6,9,9,10,10,11,11,12,12,13,13,14,14,14-henicosafluoro-7-tetradecene (21)

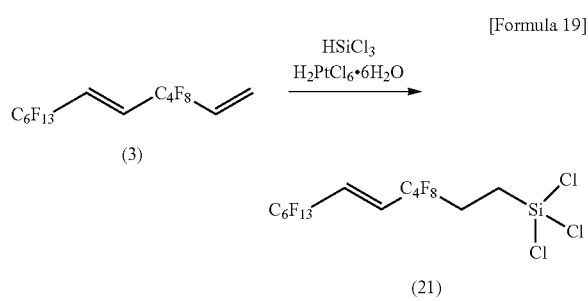

[Formula 19]

A glass pressure-resistant tube (manufactured by Ace Glass Inc.: 40 ml) was charged with 1.00 g (1.7 mmol) of compound (3), 0.004 g (0.01 mmol) of chloroplatinic acid hexahydrate (reagent of Wako Pure Chemical Industries, Ltd.) and 0.45 g (3.3 mmol) of trichlorosilane (reagent of Tokyo Chemical Industry Co., Ltd.), and the reaction was performed under stirring at 50° C. for 3 days.

After the reaction, excessive trichlorosilane was removed by nitrogen bubbling, and thereafter Kugelrohr distillation was performed to obtain 0.72 g of colorless liquid compound (21). The yield was 42.7%.

$^1$H-NMR (solvent: deuterochloroform, internal standard: tetramethylsilane) δ (ppm): 6.45 (m, 2H, —C$\underline{H}$=C$\underline{H}$—), 2.29 (m, 2H, CF$_2$C$\underline{H}_2$), 1.65 (m, 2H, C$\underline{H}_2$—Si)

$^{19}$F-NMR (solvent: deuterochloroform, internal standard: trifluoromethylbenzene) δ (ppm): −81.34 (s, 3F, CF$_3$), −114.3-−114.6 (m, 4F, C$\underline{F}_2$CH=), −116.13 (t, 2F, C$\underline{F}_2$CH$_2$), −122.08 (s, 2F, CF$_2$), −123.30 (b, 4F, CF$_2$), −123.6-123.9 (m, 4F, CF$_2$), −126.64 (s, 2F, CF$_3$—C$\underline{F}_2$)

Example 9

Synthesis of 1-[3-(triethoxysilyl)-propyl]carbamoyloxy-4,4,5,5,6,6,7,7,8,8,9,9,12,12,13,13,14,14,15,15,15-henicosafluoro-10-pentadecene (22)

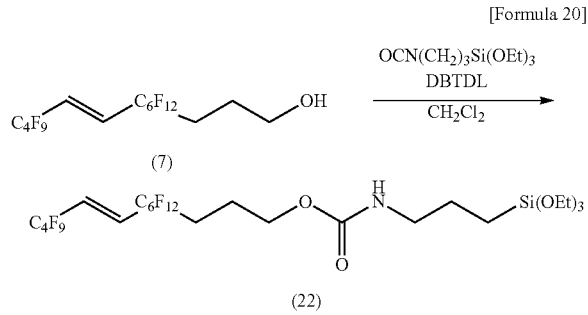

[Formula 20]

In 4 g of dichloromethane were dissolved 4.00 g (6.62 mmol) of compound (7) and 1.72 g (6.95 mmol) of 3-(triethoxysilyl)propyl isocyanate, and 0.04 g (0.07 mmol) of dibutyltin dilaurate was added thereto. The reaction was conducted with stirring at room temperature for 2 hours, and purification was performed by a silica column chromatographic method (filler: silica gel C-300 produced by Wako Pure Chemical Industries Co., Ltd., eluent: dichloromethane) to provide 5.41 g of the product of interest (22). The yield was 95.4%.

$^1$H-NMR (solvent: deuterochloroform, internal standard: tetramethylsilane) δ (ppm): 6.47 (m, 2H, C$_4$F$_9$C$\underline{H}$=C$\underline{H}$C$_6$F$_{12}$), 5.03 (t, 1H, NH), 4.12 (t, 2H, CH$_2$O), 3.81 (q, 6H, C$\underline{H}_2$CH$_3$), 3.20 (q, 2H, NHC$\underline{H}_2$), 2.22 (m, 2H, C$\underline{H}_2$CF$_2$), 2.15 (m, 2H, C$\underline{H}_2$CF$_2$), 1.91 (m, 2H, NHCH$_2$C$\underline{H}_2$CH$_2$), 1.65 (m, 2H, CF$_2$CH$_2$C$\underline{H}_2$CH$_2$), 1.23 (t, 9H, CH$_2$C$\underline{H}_3$), 0.65 (t, 2H, C$\underline{H}_2$Si)

$^{19}$F-NMR (solvent: deuterochloroform, internal standard: trifluoromethylbenzene) δ (ppm): −81.58 (t, 3F, CF$_3$), −114.51 (m, 4F, C$\underline{F}_2$CH), −114.92 (m, 2F, C$\underline{F}_2$CH$_2$), −122.15 (m, 4F, CF$_2$CF$_2$), −123.95 (m, 4F, CF$_2$CF$_2$), −124.78 (m, 2F, CF$_2$), −126.32 (m, 2F, CF$_2$)

Example 10

Synthesis of 1-[3-(triethoxysilyl)-propyl]carbamoyloxy-4,4,5,5,6,6,7,7,8,8,9,9,12,12,13,13,14,14,15,15,16,16,17,17,17-pentacosafluoro-10-heptadecene (23)

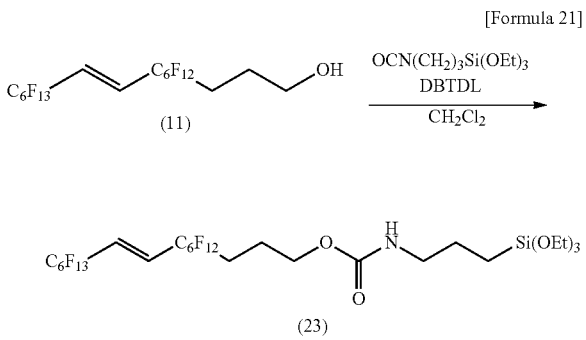

[Formula 21]

In 4 g of dichloromethane were dissolved 2.26 g (3.21 mmol) of compound (11) and 0.83 g (3.37 mmol) of 3-(triethoxysilyl)propyl isocyanate, and 0.02 g (0.03 mmol) of dibutyltin dilaurate was added thereto. The reaction was conducted with stirring at room temperature for 2 hours, and purification was performed by a silica column chromatographic method (filler: silica gel C-300 produced by Wako Pure Chemical Industries Co., Ltd., eluent: dichloromethane) to provide 2.78 g of the product of interest (23). The yield was 91.3%.

$^1$H-NMR (solvent: deuterochloroform, internal standard: tetramethylsilane) δ (ppm): 6.48 (m, 2H, C$_6$F$_{13}$C$\underline{H}$=C$\underline{H}$C$_6$F$_{12}$), 5.03 (t, 1H, NH), 4.12 (t, 2H, C$\underline{H}_2$O), 3.82 (q, 6H, C$\underline{H}_2$CH$_3$), 3.20 (q, 2H, NHC$\underline{H}_2$), 2.22 (m, 2H, C$\underline{H}_2$CF$_2$), 2.15 (m, 2H, C$\underline{H}_2$CF$_2$), 1.91 (m, 2H, NHCH$_2$C$\underline{H}_2$CH$_2$), 1.65 (m, 2H, CF$_2$CH$_2$C$\underline{H}_2$CH$_2$), 1.23 (t, 9H, CH$_2$C$\underline{H}_3$), 0.65 (t, 2H, C$\underline{H}_2$Si)

$^{19}$F-NMR (solvent: deuterochloroform, internal standard: trifluoromethylbenzene) δ (ppm): −81.35 (t, 3F, CF$_3$), −114.38 (m, 4F, C$\underline{F}_2$CH), −114.94 (m, 2F, C$\underline{F}_2$CH$_2$), −122.09 (m, 6F, CF$_2$CF$_2$CF$_2$), −123.37 (m, 2F, CF$_2$), −123.95 (m, 6F, CF$_2$CF$_2$CF$_2$), −126.67 (m, 2F, CF$_2$)

Example 11

Synthesis of 1-[3-(triethoxysilyl)-propyl]carbamoy-loxy-4,4,5,5,6,6,7,7,10,11,11,12,12,13,13,14,14,15,15,15-eicosafluoro-9-pentadecene (24)

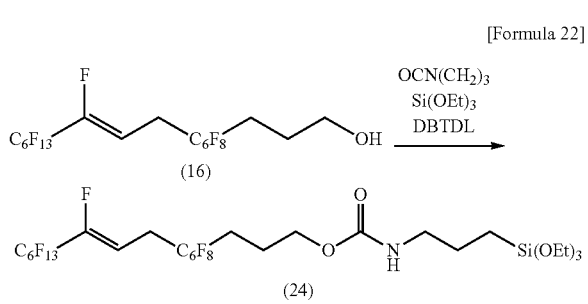

[Formula 22]

In 1 g of dichloromethane were dissolved 0.2513 g (0.41 mmol) of compound (16) and 0.1077 g (0.44 mmol) of 3-(triethoxysilyl)propyl isocyanate, and 0.0026 g (0.004 mmol) of dibutyltin dilaurate was added thereto.

The reaction was conducted with stirring at room temperature for 2 hours, and purification was performed by a silica column chromatographic method (filler: silica gel 60N produced by Kanto Kagaku, eluent: hexane) to provide 0.33 g of the product of interest (24). The yield was 93.3%.

$^1$H-NMR (solvent: deuterochloroform, internal standard: tetramethylsilane) δ (ppm): 5.67 (dt, 1H, CF=C$\underline{H}$—), 4.97 (b, 1H, —CON$\underline{H}$—), 4.05 (m, 2H, C$\underline{H_2}$O), 3.75 (q, 6H, C$\underline{H_3}$CH$_2$O), 3.11 (m, 2H, N—C$\underline{H_2}$), 3.01 (td, 2H, CF$_2$C$\underline{H_2}$CH=) 2.10 (m, 2H, CF$_2$C$\underline{H_2}$CH$_2$), 1.83 (m, 2H, CH$_2$C$\underline{H_2}$CH$_2$O), 1.56 (m, 2H, NC$\underline{H_2}$CH$_2$CH$_2$), 1.15 (9H, CH$_3$), 0.56 (m, 2H, C$\underline{H_2}$—Si)

$^{19}$F-NMR (solvent: deuterochloroform, internal standard: trifluoromethylbenzene) δ (ppm): −81.34 (t, 3F, CF$_3$), −113.07 (s, 2F, C$\underline{F_2}$—CF=), −115.11 (m, 2F, CF$_2$), −118.51 (m, 2F, CH$_2$C$\underline{F_2}$CF$_2$), −123.48 (s, 2F, CF$_2$), −123.7-124.2 (m, 6F, CF$_2$), −125.39 (s, 1F, —C$\underline{F}$=CH), −126.73 (s, 2F, CF$_3$—C$\underline{F_2}$)

Example 12

Synthesis of 1-trichlorosilyl-3,3,4,4,5,5,6,6,7,7,8,11,11,12,12,13,13,14,14,15,15,16,16,16-tetracosafluoro-8-hexadecene (25)

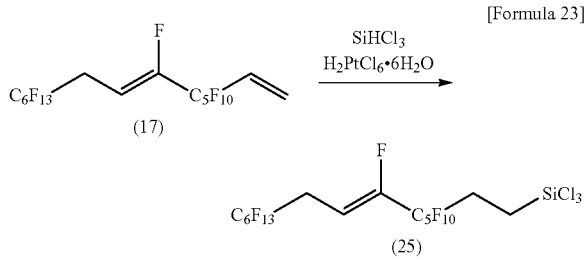

[Formula 23]

A glass pressure-resistant tube (manufactured by Ace Glass Inc.: 40 ml) was charged with 1.00 g (1.53 mmol) of compound (17), 0.008 g (0.02 mmol) of chloroplatinic acid hexahydrate (reagent of Wako Pure Chemical Industries, Ltd.) and 0.31 g (2.29 mmol) of trichlorosilane (reagent of Tokyo Chemical Industry Co., Ltd.), and the reaction was performed under stirring at 50° C. for 15 hours.

After the reaction, excessive trichlorosilane was removed by nitrogen bubbling, and thereafter Kugelrohr distillation was performed to obtain 0.54 g of yellow liquid compound (25). The yield was 44.7%.

$^1$H-NMR (solvent: deuterochloroform, internal standard: tetramethylsilane) δ (ppm): 5.71 (m, 1H, CH$_2$C$\underline{H}$CF), 3.10 (m, 2H, C$\underline{H_2}$CHCF), 2.31 (m, 2H, C$\underline{H_2}$CH$_2$Si), 1.65 (m, 2H, CH$_2$C$\underline{H_2}$Si)

$^{19}$F-NMR (solvent: deuterochloroform, internal standard: trifluoromethylbenzene) δ (ppm): −81.28 (t, 3F, CF$_3$), −112.84 (m, 2F, C$\underline{F_2}$CH$_2$CF), −116.10 (m, 2F, C$\underline{F_2}$CH$_2$CH$_2$), −118.48 (m, 2F, CF$_2$), −122.43 (m, 4F, CF$_2$CF$_2$), −123.79 (m, 8F, CF$_2$CF$_2$CF$_2$CF$_2$), −124.50 (m, 1F, CF), −126.65 (m, 2F, CF$_2$)

Example 13

Synthesis of 1-triethoxysilyl-3,3,4,4,5,5,6,6,7,7,8,11,11,12,12,13,13,14,14,15,15,16,16,16-tetracosafluoro-8-hexadecene (26)

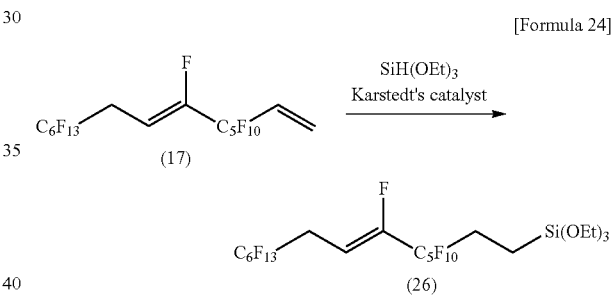

[Formula 24]

A glass pressure-resistant tube (manufactured by Ace Glass Inc.: 40 ml) was charged with 2.00 g (3.06 mmol) of compound (17), 0.012 g (0.03 mmol) of a Karstedt catalyst (reagent of Tokyo Chemical Industry Co., Ltd.) and 0.60 g (3.67 mmol) of triethoxysilane (reagent of Tokyo Chemical Industry Co., Ltd.), and the reaction was performed under stirring at 80° C. for 15 hours.

The resulting orange oily product was purified and separated by silica gel column chromatography (filler: silica gel C-300 produced by Wako Pure Chemical Industries Co., Ltd., eluent: dichloromethane/hexane=1:3) to obtain 1.19 g of compound (26). The yield was 47.5%.

$^1$H-NMR (solvent: deuterochloroform, internal standard: tetramethylsilane) δ (ppm): 5.71 (m, 1H, CH$_2$C$\underline{H}$CF) 3.84 (q, 6H, C$\underline{H_2}$CH$_3$) 3.10 (m, 2H, C$\underline{H_2}$CHCF) 3.06 (m, 2H, CH=C$\underline{H_2}$) 2.17 (m, 2H, C$\underline{H_2}$CH$_2$Si) 1.23 (t, 9H, CH$_2$C$\underline{H_3}$) 0.86 (m, 2H, CH$_2$C$\underline{H_2}$Si)

$^{19}$F-NMR (solvent: deuterochloroform, internal standard: trifluoromethylbenzene) δ (ppm): −81.36 (t, 3F, CF$_3$), −112.92 (m, 2F, C$\underline{F_2}$CH$_2$CF), −116.91 (m, 2F, C$\underline{F_2}$CH$_2$CH$_2$), −118.45 (m, 2F, CF$_2$), −122.34 (m, 4F, CF$_2$CF$_2$), −123.89 (m, 8F, CF$_2$CF$_2$CF$_2$CF$_2$), −124.49 (m, 1F, CF), −126.62 (m, 2F, CF$_2$)

Example 14

Synthesis of 1-trichlorosilyl-3,3,4,4,5,5,6,6,7,7,8,11,12,12,13,13,14,14,15,15,16,16,16-tricosafluoro-8,10-hexadecadiene (27)

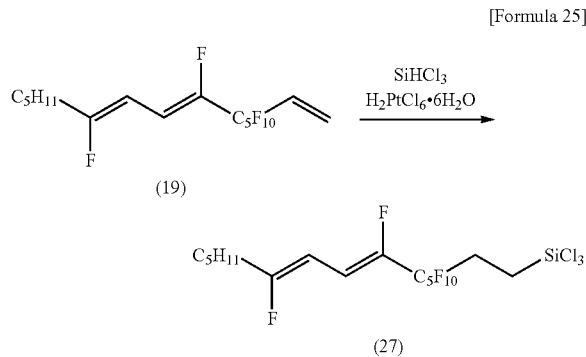

[Formula 25]

A glass pressure-resistant tube (manufactured by Ace Glass Inc.: 40 ml) was charged with 1.00 g (1.63 mmol) of compound (19), 0.008 g (0.02 mmol) of chloroplatinic acid hexahydrate (reagent of Wako Pure Chemical Industries, Ltd.) and 0.33 g (2.44 mmol) of trichlorosilane (reagent of Tokyo Chemical Industry Co., Ltd.), and the reaction was performed under stirring at 50° C. for 15 hours.

After the reaction, excessive trichlorosilane was removed by nitrogen bubbling, and thereafter Kugelrohr distillation was performed to obtain 0.31 g of yellow liquid compound (27). The yield was 25.0%.

$^1$H-NMR (solvent: deuterochloroform, internal standard: tetramethylsilane) δ (ppm): 6.48 (m, 2H, CFCH=CHCF), 2.30 (m, 2H, CH$_2$CH$_2$Si), 1.66 (m, 2H, CH$_2$CH$_2$Si)

$^{19}$F-NMR (solvent: deuterochloroform, internal standard: trifluoromethylbenzene) δ (ppm): −81.27 (m, 3F, CF$_3$), −114.39 (m, 2F, CF$_2$CH), −116.91 (m, 2F, CF$_2$CF), −118.45 (m, 2F, CF$_2$CF$_2$), −119.50 (m, 1F, CF), −120.43 (m, 1F, CF), −121.21 (m, 2F, CF$_2$), −123.34 (m, 6F, CF$_2$CF$_2$CF$_2$), −124.20 (m, 2F, CF$_2$), −126.69 (m, 2F, CF$_2$)

Example 15

Synthesis of 1-[3-(triethoxysilyl)-propyl]carbamoyloxy-3,3,4,4,5,5,6,6,7,7,8,11,12,12,13,13,14,14,15,15,16,16,16-tricosafluoro-8,10-hexadecadiene (28)

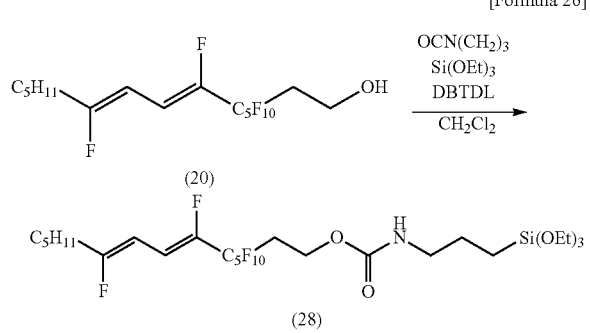

[Formula 26]

In a 5-ml eggplant flask purged with nitrogen, 1.00 g (1.53 mmol) of compound (20) and 0.38 g (1.53 mmol) of 3-(triethoxysilyl)propyl isocyanate were dissolved in 1.78 g of tetrahydrofuran, and 0.0097 g (0.02 mmol) of dibutyltin dilaurate was added thereto.

The reaction was conducted under a nitrogen atmosphere with stirring at room temperature for 65 hours, purification was performed by a silica column chromatographic method (filler: silica gel 60N produced by Kanto Kagaku, eluent: hexane-ethyl acetate 95/5 (volume/volume)) to provide 0.75 g of the compound of interest (28). The yield was 55.3%.

The resulting compound (28) was analyzed, and the following results were obtained.

$^1$H-NMR (solvent: deuterochloroform, internal standard: tetramethylsilane) δ (ppm): 6.48 (dt, 2H, CF=CH—CH=CF), 5.06 (b, 1H, —CONH—), 4.36 (t, 2H, CH$_2$O), 3.81 (q, 6H, CH$_3$CH$_2$O), 3.20 (m, 2H, N—CH$_2$), 2.43 (m, 2H, CF$_2$CH$_2$), 1.63 (m, 2H, CH$_2$CH$_2$CH$_2$O), 1.23 (t, 9H, CH$_3$), 0.64 (m, 2H, CH$_2$—Si)

$^{19}$F-NMR (solvent: deuterochloroform, internal standard: trifluoromethylbenzene) δ (ppm): −81.34 (t, 3F, CF$_3$), −114.15 (m, 2F, CF$_2$CH$_2$), −118.49 (m, 4F, CF$_2$CF=), −119.8 (m, 1F, CF=CH), −120.44 (m, 1F, CF=CH), −122.24 (m, 2F, CF$_2$), −123.36 (m, 6F, CF$_2$), −124.20 (m, 2F, CF$_2$), −126.72 (m, 2F, CF$_3$—CF$_2$)

Example 16

Synthesis of 4,4,5,5,6,6,7,7,8,8,9,9,12,12,13,13,14,14,15,15,16,16,17,17,17-pentacosafluoro-10-heptadecenyl 2-methylpropenate (29)

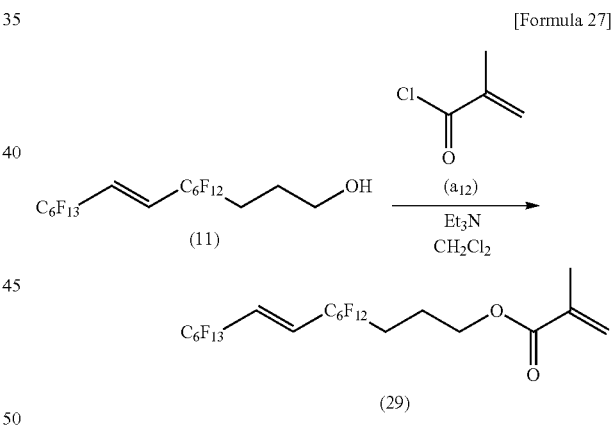

[Formula 27]

A glass pressure-resistant tube (manufactured by Ace Glass Inc.: 40 ml) was charged with 1.00 g (1.42 mmol) of compound (11), 4.7 g of dichloromethane and 0.22 g (2.13 mmol) of triethylamine (reagent of Wako Pure Chemical Industries, Ltd.), and 0.28 g (2.13 mmol) of methacryloyl chloride ($\alpha_{12}$) (reagent of Tokyo Chemical Industry Co., Ltd.) was dropped under stirring at 0° C. over 5 minutes. After the reaction was performed under stirring at room temperature for 1 hour, the solvent was removed by nitrogen bubbling, and the reaction liquid was diluted with 20 g of diisopropyl ether and washed with 20 g of saturated saline three times. The organic layer was dried with anhydrous magnesium sulfate and condensed under reduced pressure, and thereafter the resulting yellow oily product was purified and separated by silica gel column chromatography (filler: silica gel C-300 produced by Wako Pure Chemical Industries Co., Ltd., eluent: ethyl acetate/hexane=1:9) to obtain 0.70 g of compound (29). The yield was 63.8%.

$^1$H-NMR (solvent: deuterochloroform, internal standard: tetramethylsilane) δ (ppm): 6.47 (m, 2H, C$_6$F$_{13}$CH=CHC$_6$F$_{12}$), 6.11 (m, 1H, CH), 5.55 (m, 1H, CH), 4.20 (t, 2H, CH$_2$O), 2.19 (m, 2H, CH$_2$CF$_2$), 1.99 (m, 2H, CH$_2$CH$_2$CH$_2$), 1.93 (m, 3H, CH$_3$)

$^{19}$F-NMR (solvent: deuterochloroform, internal standard: trifluoromethylbenzene) δ (ppm): −81.39 (t, 3F, CF$_3$), −114.34 (m, 4F, CF$_2$CH), −114.80 (m, 2F, CF$_2$CH$_2$), −122.04 (m, 6F, CF$_2$CF$_2$CF$_2$), −123.31 (m, 2F, CF$_2$), −123.87 (m, 6F, CF$_2$CF$_2$CF$_2$), −126.64 (m, 2F, CF$_2$)

Example 17

Synthesis of 4,4,5,5,6,6,7,7,8,8,9,9,12,12,13,13,14,14,15,15,16,16,17,17,17-pentacosafluoro-10-heptadecenyl propenate (30)

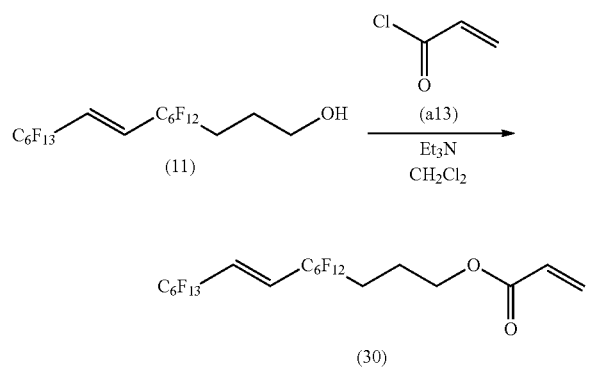

[Formula 28]

(30)

A glass pressure-resistant tube (manufactured by Ace Glass Inc.: 40 ml) was charged with 0.50 g (0.71 mmol) of compound (11), 2.4 g of dichloromethane and 0.11 g (1.07 mmol) of triethylamine (reagent of Wako Pure Chemical Industries, Ltd.), and 0.12 g (1.07 mmol) of acryloyl chloride (α$_{13}$) (reagent of Tokyo Chemical Industry Co., Ltd.) was dropped under stirring at 0° C. over 5 minutes. After the reaction was performed under stirring at room temperature for 1 hour, the solvent was removed by nitrogen bubbling, and the reaction liquid was diluted with 20 g of diisopropyl ether and washed with 20 g of saturated saline three times. The organic layer was dried with anhydrous magnesium sulfate and condensed under reduced pressure, and thereafter the resulting yellow oily product was purified and separated by silica gel column chromatography (filler: silica gel C-300 produced by Wako Pure Chemical Industries Co., Ltd., eluent: ethyl acetate/hexane=1:9) to obtain 0.11 g of compound (30). The yield was 20.4%.

$^1$H-NMR (solvent: deuterochloroform, internal standard: tetramethylsilane) δ (ppm): 6.49 (m, 2H, C$_6$F$_{13}$CH=CHC$_6$F$_{12}$), 6.45 (m, 1H, CH), 6.13 (m, 1H, CH), 5.85 (m, 1H, CH), 4.24 (t, 2H, CH$_2$O), 2.19 (m, 2H, CH$_2$CF$_2$), 2.01 (m, 2H, CH$_2$CH$_2$CH$_2$)

$^{19}$F-NMR (solvent: deuterochloroform, internal standard: trifluoromethylbenzene) δ (ppm): −81.31 (t, 3F, CF$_3$), −114.36 (m, 4F, CF$_2$CH), −114.91 (m, 2F, CF$_2$CH$_2$), −122.12 (m, 6F, CF$_2$CF$_2$CF$_2$), −123.37 (m, 2F, CF$_2$), −123.95 (m, 6F, CF$_2$CF$_2$CF$_2$), −126.65 (m, 2F, CF$_2$)

Example 18

Synthesis of 3,3,4,4,5,5,6,6,7,7,8,11,11,12,12,13,13,14,14,15,15,16,16,16-tetracosafluoro-8-hexadecenyl 2-methylpropenate (31)

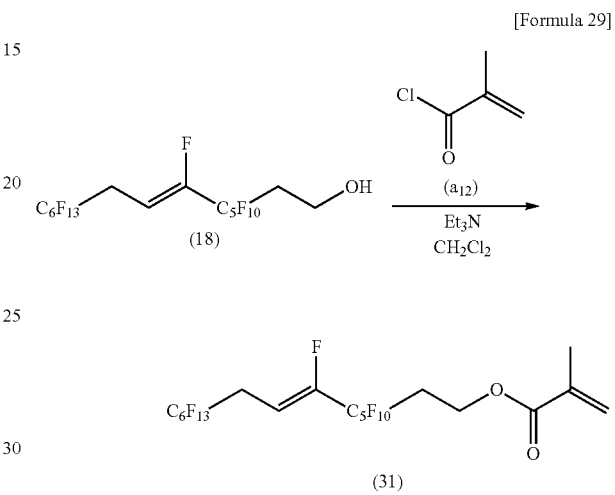

[Formula 29]

(31)

A glass pressure-resistant tube (manufactured by Ace Glass Inc.: 40 ml) was charged with 0.50 g (0.74 mmol) of compound (18), 2.5 g of dichloromethane and 0.11 g (1.12 mmol) of triethylamine (reagent of Wako Pure Chemical Industries, Ltd.), and 0.15 g (1.12 mmol) of methacryloyl chloride (α$_{12}$) (reagent of Tokyo Chemical Industry Co., Ltd.) was dropped under stirring at 0° C. over 5 minutes. After the reaction was performed under stirring at room temperature for 1 hour, the solvent was removed by nitrogen bubbling, and the reaction liquid was diluted with 20 g of diisopropyl ether and washed with 20 g of saturated saline three times. The organic layer was dried with anhydrous magnesium sulfate and condensed under reduced pressure, and thereafter the resulting yellow oily product was purified and separated by silica gel column chromatography (filler: silica gel C-300 produced by Wako Pure Chemical Industries Co., Ltd., eluent: ethyl acetate/hexane=1:9) to obtain 0.31 g of compound (31). The yield was 56.6%.

$^1$H-NMR (solvent: deuterochloroform, internal standard: tetramethylsilane) δ (ppm): 6.14 (m, 1H, CH), 5.71 (m, 1H, CH=CH$_2$), 5.60 (m, 1H, CH), 4.45 (t, 2H, CF$_2$CH$_2$CH$_2$OH), 3.09 (m, 2H, CH$_2$CHCF), 2.50 (m, 2H, CF$_2$CH$_2$CH$_2$OH), 1.95 (m, 3H, CH$_3$)

$^{19}$F-NMR (solvent: deuterochloroform, internal standard: trifluoromethylbenzene) δ (ppm): −81.37 (t, 3F, CF$_3$), −112.91 (m, 2F, CF$_2$CH), −114.13 (m, 2F, CF$_2$CH$_2$), −118.45 (m, 2F, CF$_2$), −122.36 (m, 4F, CF$_2$CF$_2$), −123.47 (m, 6F, CF$_2$CF$_2$CF$_2$), −124.18 (m, 2F, CF$_2$), −124.57 (m, 1F, CF), −126.67 (m, 2F, CF$_2$)

Example 19

Synthesis of 3,3,4,4,5,5,6,6,7,7,8,11,12,12,13,13,14,14,15,15,16,16,16-tricosafluoro-8,10-hexadecadienyl 2-methylpropenate (32)

[Formula 30]

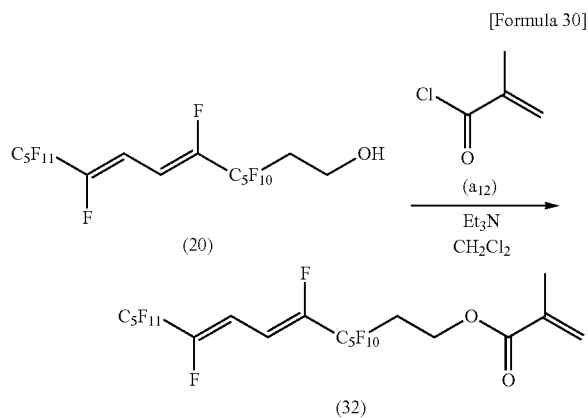

A glass pressure-resistant tube (manufactured by Ace Glass Inc.: 40 ml) was charged with 0.44 g (0.67 mmol) of compound (20), 2.2 g of dichloromethane and 0.10 g (1.01 mmol) of triethylamine (reagent of Wako Pure Chemical Industries, Ltd.), and 0.13 g (1.01 mmol) of methacryloyl chloride ($\alpha_{12}$) (reagent of Tokyo Chemical Industry Co., Ltd.) was dropped under stirring at 0° C. over 5 minutes. After the reaction was performed under stirring at room temperature for 1 hour, the solvent was removed by nitrogen bubbling, and the reaction liquid was diluted with 20 g of diisopropyl ether and washed with 20 g of saturated saline three times. The organic layer was dried with anhydrous magnesium sulfate and condensed under reduced pressure, and thereafter the resulting yellow oily product was purified and separated by silica gel column chromatography (filler: silica gel C-300 produced by Wako Pure Chemical Industries Co., Ltd., eluent: ethyl acetate/hexane=1:9) to obtain 0.24 g of compound (32). The yield was 49.7%.

$^1$H-NMR (solvent: deuterochloroform, internal standard: tetramethylsilane) δ (ppm): 6.48 (m, 2H, CF$\underline{CH}$=$\underline{CH}$CF), 6.14 (m, 1H, $\underline{CH}$=CH$_2$), 5.61 (m, 1H, CH), 4.45 (t, 2H, CF$_2$CH$_2$$\underline{CH_2}$OH), 2.51 (m, 2H, CF$_2$$\underline{CH_2}$CH$_2$OH), 1.95 (m, 3H, CH$_3$)

$^{19}$F-NMR (solvent: deuterochloroform, internal standard: trifluoromethylbenzene) δ (ppm): −81.27 (m, 3F, CF$_3$), −114.13 (m, 2F, $\underline{CF_2}$CH), −118.46 (m, 4F, $\underline{CF_2}$CF), −119.59 (m, 1F, CF), −120.32 (m, 1F, CF), −122.23 (m, 2F, CF$_2$), −123.35 (m, 6F, CF$_2$CF$_2$CF$_2$), −124.17 (m, 2F, CF$_2$), −126.669 (m, 2F, CF$_2$)

Example 20

Synthesis of 4,4,5,5,6,6,7,7,8,8,9,9,12,12,13,13,14,14,15,15,16,16,17,17,17-pentacosafluoro-10-heptadecenyl phosphate (33)

[Formula 31]

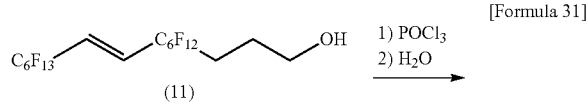

A 50-ml two-necked flask was charged with 1.96 g (12.78 mmol) of phosphorus oxychloride (reagent of Wako Pure Chemical Industries, Ltd.) and 2.00 g (2.84 mmol) of compound (11), and the reaction was performed under stirring at 80° C. for 3 hours. The reaction liquid was dropped to 20 g of water, and extracted with 30 g of chloroform. The aqueous layer was subjected to decantation, and the organic layer was washed with saturated saline and extracted with 50 g of acetone. The organic layer was condensed under reduced pressure, thereafter the resulting yellow oily product was dissolved in 20 g of acetone, and a precipitate was removed by suction filtration. The filtrate was condensed under reduced pressure to obtain 1.65 g of compound (33). The yield was 74.1%.

$^1$H-NMR (solvent: deuterochloroform, internal standard: tetramethylsilane) δ (ppm): 6.51 (m, 2H, C$_6$F$_{13}$ $\underline{CH}$=$\underline{CH}$C$_6$F$_{12}$), 4.44 (m, 2H, $\underline{CH_2}$OP), 2.32 (m, 2H, $\underline{CH_2}$CF$_2$), 2.13 (m, 2H, CH$_2$$\underline{CH_2}$CH$_2$)

$^{19}$F-NMR (solvent: deuterochloroform, internal standard: trifluoromethylbenzene) δ (ppm): −81.73 (t, 3F, CF$_3$), −114.00 (m, 4F, $\underline{CF_2}$CH), −114.86 (m, 2F, $\underline{CF_2}$CH$_2$), −122.21 (m, 6F, CF$_2$CF$_2$CF$_2$), −123.51 (m, 2F, CF$_2$), −123.94 (m, 6F, CF$_2$CF$_2$CF$_2$), −126.86 (m, 2F, CF$_2$)

Example 21

Synthesis of diethyl 4,4,5,5,6,6,7,7,8,8,9,9,12,12,13,13,14,14,15,15,16,16,17,17,17-pentacosafluoro-10-heptadecenyl phosphate (34)

[Formula 32]

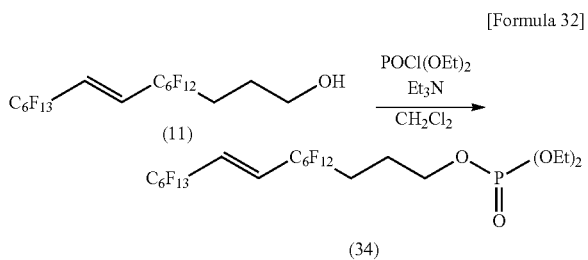

A glass pressure-resistant tube (manufactured by Ace Glass Inc.: 40 ml) was charged with 1.00 g (1.42 mmol) of compound (11), 4.7 g of dichloromethane and 0.43 g (4.26 mmol) of triethylamine (reagent of Wako Pure Chemical Industries, Ltd.), and 0.74 g (4.26 mmol) of diethyl chlorophosphate (reagent of Tokyo Chemical Industry Co., Ltd.) was dropped under stirring at 0° C. over 5 minutes. After the reaction was performed under stirring at room temperature for 1 hour, the solvent was removed by nitrogen bubbling, and the reaction liquid was diluted with 20 g of diisopropyl ether and washed with 20 g of saturated saline three times. The organic layer was dried with anhydrous magnesium sulfate and condensed under reduced pressure, and thereafter the resulting yellow oily product was purified and separated by silica gel column chromatography (filler: silica gel C-300 produced by Wako Pure Chemical Industries Co., Ltd., eluent: ethyl acetate/hexane=1:1) to obtain 1.02 g of compound (34). The yield was 85.5%.

$^1$H-NMR (solvent: deuterochloroform, internal standard: tetramethylsilane) δ (ppm): 6.48 (m, 2H, C$_6$F$_{13}$CH=CHC$_6$F$_{12}$), 4.14 (m, 2H, CH$_2$OP), 4.12 (m, 4H, CH$_2$CH$_3$), 2.23 (m, 2H, CH$_2$CF$_2$), 1.98 (m, 2H, CH$_2$CH$_2$CH$_2$), 1.33 (m, 6H, CH$_2$CH$_3$)

$^{19}$F-NMR (solvent: deuterochloroform, internal standard: trifluoromethylbenzene) δ (ppm): −81.35 (t, 3F, CF$_3$), −114.33 (m, 4F, CF$_2$CH), −114.83 (m, 2F, CF$_2$CH$_2$), −122.04 (m, 6F, CF$_2$CF$_2$CF$_2$), −123.32 (m, 2F, CF$_2$), −123.85 (m, 6F, CF$_2$CF$_2$CF$_2$), −126.68 (m, 2F, CF$_2$)

Example 22

Synthesis of diethyl 3,3,4,4,5,5,6,6,7,7,8,11,11,12,12,13,13,14,14,15,15,16,16,16-tetracosafluoro-8-hexadecenyl phosphate (35)

[Formula 33]

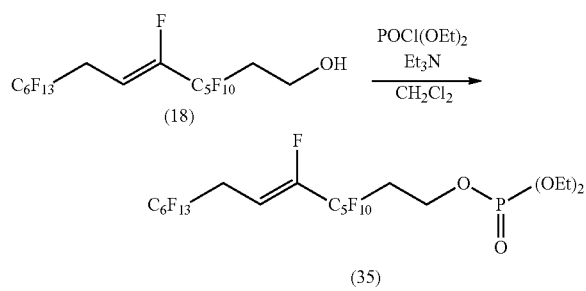

A glass pressure-resistant tube (manufactured by Ace Glass Inc.: 40 ml) was charged with 0.50 g (0.74 mmol) of compound (18), 2.5 g of dichloromethane and 0.23 g (2.23 mmol) of triethylamine (reagent of Wako Pure Chemical Industries, Ltd.), and 0.39 g (2.23 mmol) of diethyl chlorophosphate (reagent of Tokyo Chemical Industry Co., Ltd.) was dropped under stirring at 0° C. over 5 minutes. After the reaction was performed under stirring at room temperature for 1 hour, the solvent was removed by nitrogen bubbling, and the reaction liquid was diluted with 20 g of diisopropyl ether and washed with 20 g of saturated saline three times. The organic layer was dried with anhydrous magnesium sulfate and condensed under reduced pressure, and thereafter the resulting yellow oily product was purified and separated by silica gel column chromatography (filler: silica gel C-300 produced by Wako Pure Chemical Industries Co., Ltd., eluent: ethyl acetate/hexane=1:1) to obtain 0.51 g of compound (35). The yield was 85.3%.

$^1$H-NMR (solvent: deuterochloroform, internal standard: tetramethylsilane) δ (ppm): 5.71 (m, 1H, CH=CH$_2$), 4.33 (q, 2H, CF$_2$CH$_2$CH$_2$OH), 4.13 (m, 4H, CH$_2$OP), 3.09 (m, 2H, CH$_2$CHCF), 2.53 (m, 2H, CF$_2$CH$_2$CH$_2$OH), 1.35 (m, 6H, CH$_2$CH$_3$)

$^{19}$F-NMR (solvent: deuterochloroform, internal standard: trifluoromethylbenzene) δ (ppm): −81.28 (t, 3F, CF$_3$), −112.91 (m, 2F, CF$_2$CH), −114.17 (m, 2F, CF$_2$CH$_2$), −118.47 (m, 2F, CF$_2$CF$_2$), −122.41 (m, 4F, CF$_2$CF$_2$), −123.47 (m, 6F, CF$_2$CF$_2$CF$_2$), −124.28 (m, 2F, CF$_2$), −124.57 (m, 1F, CF), −126.66 (m, 2F, CF$_2$)

Example 23

Synthesis of diethyl 3,3,4,4,5,5,6,6,7,7,8,11,12,12,13,13,14,14,15,15,16,16,16-tricosafluoro-8,10-hexadecadienyl phosphate (36)

[Formula 34]

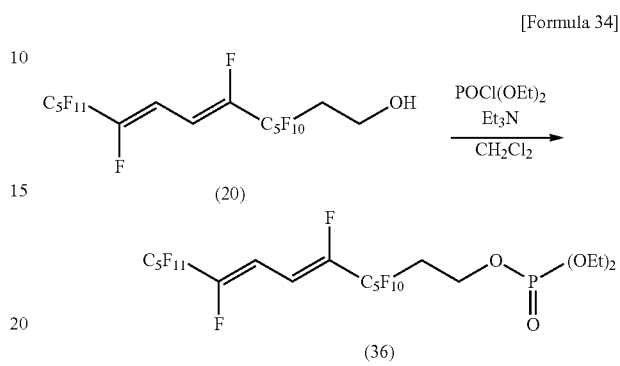

A glass pressure-resistant tube (manufactured by Ace Glass Inc.: 40 ml) was charged with 0.25 g (0.39 mmol) of compound (20), 1.3 g of dichloromethane and 0.12 g (1.18 mmol) of triethylamine (reagent of Wako Pure Chemical Industries, Ltd.), and 0.39 g (2.23 mmol) of diethyl chlorophosphate (reagent of Tokyo Chemical Industry Co., Ltd.) was dropped under stirring at 0° C. over 5 minutes. After the reaction was performed under stirring at room temperature for 1 hour, the solvent was removed by nitrogen bubbling, and the reaction liquid was diluted with 20 g of diisopropyl ether and washed with 20 g of saturated saline three times. The organic layer was dried with anhydrous magnesium sulfate and condensed under reduced pressure, and thereafter the resulting yellow oily product was purified and separated by silica gel column chromatography (filler: silica gel C-300 produced by Wako Pure Chemical Industries Co., Ltd., eluent: ethyl acetate/hexane=1:1) to obtain 0.26 g of compound (36). The yield was 86.5%.

$^1$H-NMR (solvent: deuterochloroform, internal standard: tetramethylsilane) δ (ppm): 6.49 (m, 2H, CFCH=CHCF), 4.33 (t, 2H, CF$_2$CH$_2$CH$_2$OH), 4.14 (m, 4H, CH$_2$OP), 2.54 (m, 2H, CF$_2$CH$_2$CH$_2$OH), 1.35 (m, 6H, CH$_2$CH$_3$)

$^{19}$F-NMR (solvent: deuterochloroform, internal standard: trifluoromethylbenzene) δ (ppm): −81.28 (m, 3F, CF$_3$), −114.15 (m, 2F, CF$_2$CH), −118.46 (m, 4F, CF$_2$CF), −119.63 (m, 1F, CF), −120.29 (m, 1F, CF), −122.24 (m, 2F, CF$_2$), −123.35 (m, 6F, CF$_2$CF$_2$CF$_2$), −124.23 (m, 2F, CF$_2$), −126.69 (m, 2F, CF$_2$)

Comparative Example 1

Synthesis of 3,3,4,4,5,5,6,6,7,7,8,8,8-tridecafluorooctyl phosphate (37)

[Formula 35]

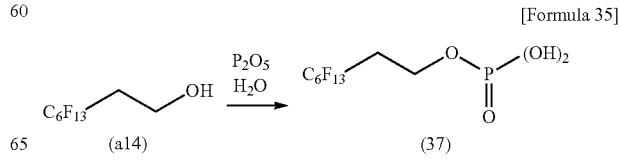

Synthesis was made based on the method described in Patent Document 4 (Japanese Patent Laid-Open No. 2015-71552). After 32.7 g (225.7 mmol) of phosphorus pentoxide, 118.7 g of 1,1,1,2,2,3,3,4,4,5,5,6,6-tridecafluorooctane and 23.2 g of 85% by mass phosphoric acid (100.5 mmol of phosphorus pentoxide and 495.1 mmol of water) were added to a 500-ml three-necked flask at room temperature (25° C.), stirring was performed for 10 minutes and thereafter 118.7 g (326.2 mmol) of perfluorohexylethyl alcohol ($\alpha_{14}$) was added thereto. An oil bath was heated to 50° C. and the reaction was conducted under stirring at the same temperature for 24 hours. Next, the oil bath was heated to 60° C., the reaction was conducted under stirring at the same temperature for 24 hours, thereafter the solvent was removed, and 150 g of ethyl acetate was newly added for dissolution. The same amount of water was added thereto, the resultant was washed with water under stirring, and an operation for removal of water used was performed three times in total. Thereafter, the solvent was removed, and the resultant was dried to provide 145 g of white powdery compound (37). The yield was 93.5 mol %.

Example 24

Glass Modification Conditions

A glass slide (manufactured by Matsunami Glass Ind., Ltd., size: 76 mm×26 mm×1.2 mm)) was immersed in a saturated potassium hydroxide-isopropyl alcohol solution at room temperature for 17 hours, washed with water and dried at 60° C. for 2 hours before use, and the resultant was immediately used as a pre-treated glass.

This pre-treated glass was treated with being stirred and immersed in a surface modifier solution, in which compound (21) synthesized in Example 8 was dissolved in a chloroform solvent so as to be in an amount of 0.3% by weight, at 50° C. for 2 hours. The glass was taken out from the modification solution, an excessive surface modifier attached to the glass surface was wiped off by Novec (registered trademark) 7100 (produced by 3M) and water, and thereafter the resultant was treated at 150° C. for 2 hours to provide a surface-modified glass substrate.

Contact Angle Measurement

Contact angle measurement was performed using the following instrument and method.

Instrument: VHX-500F (manufactured by Keyence Corporation)

Method: the contact angle was determined by dropping 1 μL of a droplet onto the surface of the surface-modified glass substrate, imaging the resultant as viewed edge-on, and subjecting the resulting projected image to a θ/2 method.

Example 25

The contact angle was measured by using compound (22) synthesized in Example 9 instead of compound (21) to modify the surface of the glass slide in the same manner as in Example 24.

Example 26

The contact angle was measured by using compound (23) synthesized in Example 10 instead of compound (21) to modify the surface of the glass slide in the same manner as in Example 24.

Example 27

The contact angle was measured by using compound (24) synthesized in Example 11 instead of compound (21) to modify the surface of the glass slide in the same manner as in Example 24.

Example 28

The contact angle was measured by using compound (25) synthesized in Example 12 instead of compound (21) to modify the surface of the glass slide in the same manner as in Example 24.

Example 29

The contact angle was measured by using compound (26) synthesized in Example 13 instead of compound (21) to modify the surface of the glass slide in the same manner as in Example 24.

Example 30

The contact angle was measured by using compound (27) synthesized in Example 14 instead of compound (21) to modify the surface of the glass slide in the same manner as in Example 24.

Example 31

The contact angle was measured by using compound (28) synthesized in Example 15 instead of compound (21) to modify the surface of the glass slide in the same manner as in Example 24.

Comparative Example 2

The contact angle was measured by using $CF_3(CF_2)_5CH_2CH_2Si(OMe)_3$ (produced by Sigma-Aldrich) as a comparative agent instead of compound (21) to modify the surface of the glass slide in the same manner as in Example 24.

The results obtained were shown in Table 1.

TABLE 1

| | Fluorine-containing compound | Contact angle [°] | |
|---|---|---|---|
| | | Water | Hexadecane |
| Example 24 | Compound (21) | 109.5 | 76.0 |
| Example 25 | Compound (22) | 97.3 | 60.4 |
| Example 26 | Compound (23) | 105.7 | 63.5 |
| Example 27 | Compound (24) | 100.1 | 49.8 |
| Example 28 | Compound (25) | 110.6 | 75.7 |
| Example 29 | Compound (26) | 104.5 | 66.7 |
| Example 30 | Compound (27) | 103.3 | 67.1 |
| Example 31 | Compound (28) | 109.4 | 64.4 |
| Comparative Example 2 | Comparative agent | 55.1 | 33.9 |

Example 32

Synthesis of Polymer 1

A 50-ml three-necked flask was charged with 0.52 g (5.18 mmol) of methyl methacrylate (reagent of Tokyo Chemical Industry Co., Ltd.), 1.00 g (1.29 mmol) of compound (29), 0.016 g (0.06 mmol) of 2,2'-azobis(2,4-dimethylvaleronitrile) (reagent of Wako Pure Chemical Industries, Ltd.) and 2.9 g of 2-butanone, purged with nitrogen by allowing nitrogen to flow into for 5 minutes with stirring, and thereafter stirred at 80° C. for 7 hours. The reaction liquid was dropped to 42.4 g of hexane to precipitate a polymer, and the supernatant solution was subjected to decantation. The remaining precipitate was again dissolved in 3.5 g of tetrahydrofuran, and the solution was added to 42.4 g of hexane to reprecipitate a polymer. The precipitate was subjected to suction filtration, and dried in vacuum to provide 0.92 g of the product of interest (polymer 1) as a white powder. The yield was 60.5%. The weight average molecular weight Mw and the dispersibility Mw/Mn of the resulting product of interest, in terms of polystyrene measured by GPC, were 17,000 and 1.5, respectively.

Example 33

Synthesis of Polymer 2

A 50-ml three-necked flask was charged with 0.53 g (5.28 mmol) of methyl methacrylate (reagent of Tokyo Chemical Industry Co., Ltd.), 1.00 g (1.32 mmol) of compound (30), 0.017 g (0.07 mmol) of 2,2'-azobis(2,4-dimethylvaleronitrile) (reagent of Wako Pure Chemical Industries, Ltd.) and 2.9 g of 2-butanone, purged with nitrogen by allowing nitrogen to flow into for 5 minutes with stirring, and thereafter stirred at 80° C. for 7 hours. The reaction liquid was dropped to 42.4 g of hexane to precipitate a polymer, and the supernatant solution was subjected to decantation. The remaining precipitate was again dissolved in 3.5 g of tetrahydrofuran, and the solution was added to 42.4 g of hexane to reprecipitate a polymer. The precipitate was subjected to suction filtration, and dried in vacuum to provide 0.95 g of the product of interest (polymer 2) as a white powder. The yield was 61.7%. The weight average molecular weight Mw and the dispersibility Mw/Mn of the resulting product of interest, in terms of polystyrene measured by GPC, were 32,000 and 2.0, respectively.

Example 34

Synthesis of Polymer 3

A 50-ml three-necked flask was charged with 0.54 g (5.40 mmol) of methyl methacrylate (reagent of Tokyo Chemical Industry Co., Ltd.), 1.00 g (1.35 mmol) of compound (31), 0.017 g (0.07 mmol) of 2,2'-azobis(2,4-dimethylvaleronitrile) (reagent of Wako Pure Chemical Industries, Ltd.) and 2.9 g of 2-butanone, purged with nitrogen by allowing nitrogen to flow into for 5 minutes with stirring, and thereafter stirred at 80° C. for 7 hours. The reaction liquid was dropped to 42.4 g of hexane to precipitate a polymer, and the supernatant solution was subjected to decantation. The remaining precipitate was again dissolved in 3.5 g of tetrahydrofuran, and the solution was added to 42.4 g of hexane to reprecipitate a polymer. The precipitate was subjected to suction filtration, and dried in vacuum to provide 0.85 g of the product of interest (polymer 3) as a white powder. The yield was 55.2%. The weight average molecular weight Mw and the dispersibility Mw/Mn of the resulting product of interest, in terms of polystyrene measured by GPC, were 18,000 and 1.7, respectively.

Example 35

Synthesis of Polymer 4

A 50-ml three-necked flask was charged with 0.53 g (5.25 mmol) of methyl methacrylate (reagent of Tokyo Chemical Industry Co., Ltd.), 1.00 g (1.28 mmol) of compound (32), 0.017 g (0.07 mmol) of 2,2'-azobis(2,4-dimethylvaleronitrile) (reagent of Wako Pure Chemical Industries, Ltd.) and 2.9 g of 2-butanone, purged with nitrogen by allowing nitrogen to flow into for 5 minutes with stirring, and thereafter stirred at 80° C. for 7 hours. The reaction liquid was dropped to 42.4 g of hexane to precipitate a polymer, and the supernatant solution was subjected to decantation. The remaining precipitate was again dissolved in 3.5 g of tetrahydrofuran, and the solution was added to 42.4 g of hexane to reprecipitate a polymer. The precipitate was subjected to suction filtration, and dried in vacuum to provide 0.81 g of the product of interest (polymer 4) as a white powder. The yield was 52.6%. The weight average molecular weight Mw and the dispersibility Mw/Mn of the resulting product of interest, in terms of polystyrene measured by GPC, were 19,000 and 1.6, respectively.

Comparative Example 3

Synthesis of Polymer 5

A 50-ml three-necked flask was charged with 1.85 g (18.51 mmol) of methyl methacrylate (reagent of Tokyo Chemical Industry Co., Ltd.), 2.00 g (4.63 mmol) of 3,3,4,4,5,5,6,6,7,7,8,8,8-tridecafluoro-n-octyl 2-methylpropenate (reagent of Tokyo Chemical Industry Co., Ltd.), 0.057 g (0.23 mmol) of 2,2'-azobis(2,4-dimethylvaleronitrile) (reagent of Wako Pure Chemical Industries, Ltd.) and 6.17 g of 2-butanone, purged with nitrogen by allowing nitrogen to flow into for 5 minutes with stirring, and thereafter stirred at 80° C. for 7 hours. The reaction liquid was dropped to 151.5 g of hexane to precipitate a polymer, and the supernatant solution was subjected to decantation. The remaining precipitate was again dissolved in 12.5 g of tetrahydrofuran, and the solution was added to 151.5 g of hexane to reprecipitate a polymer. The precipitate was subjected to suction filtration, and dried in vacuum to provide 2.01 g of the product of interest (polymer 5) as a white powder. The yield was 52.2%. The weight average molecular weight Mw and the dispersibility Mw/Mn of the resulting product of interest, in terms of polystyrene measured by GPC, were 21,000 and 2.0, respectively.

Example 36

Evaluation of Physical Properties of Polymer

In 4.75 g of 2-butanone was dissolved 0.25 g of polymer 1 obtained in Example 32, and subjected to filtration by a filter, to prepare a polymer solution. A glass substrate (50 mm×50 mm×1.0 mm) was spin-coated with the polymer solution (slope for 5 seconds, then at 1,500 rpm for 10 seconds, and slope for additional 5 seconds), and a heat treatment at 120° C. for 1 hour was performed to thereby evaporate the solvent, to form a film. The contact angle of the resulting thin film to each of water and hexadecane was measured.

Example 37

A thin film was formed in the same manner as in Example 36 by use of polymer 2 synthesized in Example 33 instead of polymer 1, and the contact angle thereof was measured.

Example 38

A thin film was formed in the same manner as in Example 36 by use of polymer 3 synthesized in Example 34 instead of polymer 1, and the contact angle thereof was measured.

Example 39

A thin film was formed in the same manner as in Example 36 by use of polymer 4 synthesized in Example 35 instead of polymer 1, and the contact angle thereof was measured.

Comparative Example 4

A thin film was formed in the same manner as in Example 36 by use of polymer 5 synthesized in Comparative Example 3 instead of polymer 1, and the contact angle thereof was measured.

The results obtained were shown in Table 2.

TABLE 2

| | Fluorine-containing polymer | Contact angle [°] Water | Hexadecane |
|---|---|---|---|
| Example 36 | Polymer 1 | 112.1 | 65.9 |
| Example 37 | Polymer 2 | 115.6 | 68.3 |
| Example 38 | Polymer 3 | 111.0 | 64.3 |
| Example 39 | Polymer 4 | 110.4 | 63.6 |
| Comparative Example 4 | Polymer 5 | 106.9 | 61.0 |

Example 40

Preparation of Release Agent Solution

An aqueous release agent solution including 0.5% by weight of compound (33) obtained in Example 20, 49.8% by weight of pure water and 49.7% by weight of isopropanol was prepared. The release agent solution was used to perform evaluation of releasability according to the following measurement method.

Evaluation of Releasability

A polyurethane prepolymer and a curing agent were poured into a mold (made of aluminum, 60 mm in diameter and 50 mm in depth) coated with the release agent, and cured under a heated and pressurized condition, and thereafter the load at which a molded product was released from the mold was measured by a push-pull scale. The releasability in a case where the load required was less than 10 N was rated as "Excellent", that in a case where the load was 10 N or more and less than 20 N was rated as "Good", that in a case where the load was 20 N or more and less than 50 N rated as "Fair", and that in a case where the load was 50 N or more was rated as "Poor". In addition, the number of times where releasing was possible under a load of less than 50 N under the same condition was measured and defined as the repeatability.

Examples 41 to 44

Each aqueous release agent solution in which the release agent compound, the amount of the additive and the amount of the solvent in Example 40 were variously changed was used to measure the same measurement.

Comparative Examples 5 to 6

Each aqueous release agent solution in which the release agent compound, the amount of the additive and the amount of the solvent in Example 40 were variously changed was used to measure the same measurement.

The results obtained were shown, together with the amount of each release agent solution component (unit: % by weight), in Table 3.

TABLE 3

| | Release agent compound | Release agent concentration | Pure water | Isopropanol | Triethylamine | Releasability | Repeatability (times) |
|---|---|---|---|---|---|---|---|
| Example 40 | Compound (33) | 0.5 | 49.8 | 49.7 | 0 | Excellent | 20 |
| Example 41 | Compound (33) | 0.5 | 99.45 | 0 | 0.05 | Excellent | 10 |
| Example 42 | Compound (34) | 0.5 | 49.8 | 49.7 | 0 | Good | 6 |
| Example 43 | Compound (35) | 0.5 | 49.8 | 49.7 | 0 | Good | 4 |
| Example 44 | Compound (36) | 0.5 | 49.8 | 49.7 | 0 | Good | 5 |
| Comparative Example 5 | Compound (37) | 0.5 | 49.8 | 49.7 | 0 | Fair | 1 |
| Comparative Example 6 | Compound (37) | 0.5 | 99.45 | 0 | 0.05 | Poor | 0 |

INDUSTRIAL APPLICABILITY

The novel fluorine-containing compound and the surface modifier using the compound, of the present invention, exhibit high water repellency and oil repellency, and can be utilized in surface modifiers such as a release agent and a antifouling agent.

The invention claimed is:

1. A fluorine-containing compound represented by the following general formula (1) or the following general formula (2):

$$Rf^1-(CR^1=CR^2-X-Rf^2)_n-Y-Z \quad (1)$$

$$Rf^1-(X-CR^1=CR^2-Rf^2)_n-Y-Z \quad (2)$$

wherein in the formula (1) or in the formula (2),
$Rf^1$ represents a perfluoroalkyl group having 1 to 6 carbon atoms, with a $CF_3$ terminal,
$Rf^2$ represents a perfluoroalkylene group having 1 to 6 carbon atoms,
in the formula (1) $R^1$ and $R^2$ represent a hydrogen atom and X is absent,
in the formula (1) $R^1$ represents a fluorine atom, $R^2$ represents a hydrogen atom and X represents $CH_2$, or
in the formula (2) $R^1$ represents a hydrogen atom, $R^2$ represents a fluorine atom and X represents $CH_2$,
n represents an integer of 1 to 5, Y is represented by the following general formula (8):

$$(CH_2)_l—Q—(CH_2)_m \quad (8)$$

wherein in the formula (8), the sum of l and m is an integer of 2 to 6,
when l and/or m represents 2 or more, a —CH=CH— structure is optionally included instead of —CH2CH2—; and
Q is absent in the formula (8), or represents —OCONH—, —CONH—, —O—, —NH—, —CO—O—, —O—CO—, —NHCONH— or —$C_6H_4$—, and
Z represents any structure of the following (i) to (iii):
(i) a structure represented by the following general formula (3) or the following general formula (4):

$$—P(=O)(OM^1)(OM^2) \quad (3)$$

$$—O—P(=O)(OM^1)(OM^2) \quad (4)$$

wherein in the formula (3) or in the formula (4), $M^1$ and $M^2$ each independently represent a hydrogen atom, an ammonium salt, an organic amine salt, or an alkyl group having 1 to 4 carbon atoms;
(ii) a vinyl group, an allyl group, a styryl group, a methacryloyl group, or an acryloyl group; or
(iii) $SiL_kL'_{(3-k)}$ wherein L represents a hydrolyzable group or a hydroxyl group, L' represents a hydrocarbon group having 1 to 6 carbon atoms, k represents an integer of 1 to 3, and, the L and L' groups may be different from or the same as each other.

2. The fluorine-containing compound according to claim 1, wherein $Rf^2$ represents a linear perfluoroalkylene group having 1 to 6 carbon atoms.

3. The fluorine-containing compound according to claim 1, wherein $R^1$ and/or $R^2$ represent(s) a hydrogen atom.

4. The fluorine-containing compound according to claim 1, wherein the hydrolyzable group L represents Cl or $OR^5$ wherein $R^5$ represents an alkyl group having 1 to 4 carbon atoms.

5. A surface modifier comprising the fluorine-containing compound according to claim 1.

6. A fluorine-containing compound represented by the following general formula (5):

$$Rf^3—(CF=CR^3—CR^4=CF—Rf^4)_n—Y—Z \quad (5)$$

wherein in the formula (5),
$Rf^3$ represents a perfluoroalkyl group having 1 to 5 carbon atoms, with a $CF_3$ terminal,
$Rf^4$ represents a perfluoroalkylene group having 1 to 5 carbon atoms,
$R^3$ and $R^4$ each independently represent a hydrogen atom or a fluorine atom,
n represents an integer of 1 to 5,
Y is represented by the following general formula (8):

$$(CH_2)_l—Q—(CH_2)_m \quad (8)$$

wherein in the formula (8), the sum of l and m is an integer of 2 to 6,
when l and/or m represents 2 or more, a —CH=CH— structure is optionally included instead of —$CH_2CH_2$—; and
Q is absent in the formula (8), or represents —OCONH—, —CONH—, —O—, —NH—, —CO—O—O—CO—, —NHCONH— or —$C_6H_4$—, and
Z represents any structure of the following (i) to (iii):
(i) a structure represented by the following general formula (6) or the following general formula (7):

$$—P(=O)(OM^3)(OM^4) \quad (6)$$

$$—O—P(=O)(OM^3)(OM^4) \quad (7)$$

wherein in the formula (6) or in the formula (7), $M^3$ and $M^4$ each independently represent a hydrogen atom, an ammonium salt, an organic amine salt, or an alkyl group having 1 to 4 carbon atoms;
(ii) a vinyl group, an allyl group, a styryl group, a methacryloyl group, or an acryloyl group; or
(iii) $SiL_kL'_{(3-k)}$ wherein L represents a hydrolyzable group or a hydroxyl group, L' represents a hydrocarbon group having 1 to 6 carbon atoms, k represents an integer of 1 to 3, and, the L and L' groups may be different from or the same as each other.

7. The fluorine-containing compound according to claim 6, wherein $Rf^4$ represents a linear perfluoroalkylene group having 1 to 5 carbon atoms.

8. The fluorine-containing compound according to claim 6, wherein $R^3$ and/or $R^4$ represent(s) a hydrogen atom.

9. The fluorine-containing compound according to claim 6, wherein the hydrolyzable group L represents Cl or $OR^5$ wherein $R^5$ represents an alkyl group having 1 to 4 carbon atoms.

10. A surface modifier comprising the fluorine-containing polymer according to claim 6.

11. A fluorine-containing polymer represented by the following general formula (1) or the following general formula (2):

$$Rf^1—(CR^1=CR^2—X—Rf^2)_n—Y—Z \quad (1)$$

$$Rf^1—(X—CR^1=CR^2—Rf^2)_n—Y—Z \quad (2)$$

wherein Z in general formula (1) or (2) comprises a repeating unit that is a vinyl group, an allyl group, a styryl group, a methacryloyl group, or an acryloyl group and that is derived from a monomer A,
wherein the monomer A is the fluorine-containing compound according to claim 1,
wherein in the formula (1) or in the formula (2), $Rf^1$ represents a perfluoroalkyl group having 1 to 6 carbon atoms, with a $CF_3$ terminal,
$Rf^2$ represents a perfluoroalkylene group having 1 to 6 carbon atoms,
$R^1$ and $R^2$ each independently represent a hydrogen atom or a fluorine atom,
n represents an integer of 1 to 5,
X is absent in the formula (1) or in the formula (2), or represents $CH_2$, O or S,
Y is represented by the following general formula (8):

$$(CH_2)_l—Q—(CH_2)_m \quad (8)$$

wherein in the formula (8), the sum of l and m is an integer of 2 to 6,
when l and/or m represents 2 or more, a —CH=CH— structure is optionally included instead of —$CH_2CH_2$—; and
Q is absent in the formula (8), or represents —OCONH—, —CONH—, —O—, —NH—, —CO—O—, —O—CO—, —NHCONH— or —$C_6H_4$—.

12. The fluorine-containing polymer according to claim 11, obtained by copolymerization of the monomer A with a monomer B having at least one polymerizable group in a molecule,
wherein the monomer B is the following compounds ($X_1$) to ($X_9$):
($X_1$) acrylic acid and methacrylic acid, and esters thereof: methyl, ethyl, butyl, isobutyl, t-butyl, propyl, 2-ethylhexyl, hexyl, decyl, lauryl, stearyl, isobornyl, behenyl, .beta.-hydroxyethyl, glycidyl, phenyl, benzyl and 4-cyanophenyl esters;

(X2) fatty acid vinyl esters: acetic acid, propionic acid, caprylic acid, lauric acid, stearic acid, behenic acid and the like;
(X₃) styrene-based compounds: styrene, .alpha.-methylstyrene, and p-methylstyrene;
(X4) halogenated vinyl or vinylidene compounds: vinyl fluoride, vinyl chloride, vinyl bromide, vinylidene fluoride, and vinylidene chloride;
(X₅) aliphatic allyl esters: allyl heptanoate, allyl caprate, and allyl caproate;
(X₆) vinyl alkyl ketones: vinyl methyl ketone, and vinyl ethyl ketone;
(X₇) acrvlamides: N-methylacrvlamide, N-methylolacrylamide, and N-methylolmethacrylamide;
(X₈) dienes: 2,3-dichloro-1,3-butadiene, and isoprene; and
(X₉) ethylene, acrylonitrile, polyethylene glycol (meth)acrylate, polypropylene glycol (meth)acrylate, methoxy polyethylene glycol (meth)acrylate, methoxy polypropylene glycol (meth)acrylate, vinyl alkyl ether, and isoprene.

13. The fluorine-containing polymer according to claim 12, wherein the monomer B is a (meth)acrylic acid or an ester thereof, fatty acid_vinyl ester, aliphatic allyl ester, vinyl alkyl ketone, acrylamide, diene, ethylene, acrylonitrile, or a halogen monomer.

14. The fluorine-containing polymer according to claim 11, having a weight average molecular weight of 1,000 to 200,000.

15. A surface modifier comprising the fluorine-containing polymer according to claim 11.

16. A fluorine-containing polymer represented by the following general formula (1) or the following general formula (2):

$$Rf^1-(CR^1=CR^2-X-Rf^2)_n-Y-Z \quad (1)$$

$$Rf^1-(X-CR^1=CR^2-Rf^2)_n-Y-Z \quad (2)$$

wherein Z in general formula (1) or (2) comprises a repeating unit that is a vinyl group, an allyl group, a styryl group, a methacryloyl group, or an acryloyl group and that is derived from a monomer A, wherein the monomer A is the fluorine-containing compound according to claim 8, wherein in the formula (1) or in the formula (2), $Rf^1$ represents a perfluoroalkyl group having 1 to 6 carbon atoms, with a $CF_3$ terminal, $Rf^2$ represents a perfluoroalkylene group having 1 to 6 carbon atoms, $R^1$ and $R^2$ each independently represent a hydrogen atom or a fluorine atom, n represents an integer of 1 to 5, X is absent in the formula (1) or in the formula (2), or represents $CH_2$, O or S, Y is represented by the following general formula (8):

$$(CH_2)_l-Q-(CH_2)_m \quad (8)$$

wherein in the formula (8), the sum of l and m is an integer of 2 to 6, when l and/or m represents 2 or more, a —CH=CH— structure is optionally included instead of —$CH_2CH_2$—; and Q is absent in the formula (8), or represents —OCONH—, —CONH—, —O—, —NH—, —CO—O—, —O—CO—, —NHCONH— or —$C_6H_4$—.

* * * * *